United States Patent
Zagon et al.

(10) Patent No.: US 7,122,651 B1
(45) Date of Patent: Oct. 17, 2006

(54) NUCLEIC ACID MOLECULES ENCODING OPIOID GROWTH FACTOR RECEPTORS

(76) Inventors: Ian S. Zagon, 589 Cook Ct., Hummelstown, PA (US) 17036; Patricia J. McLaughlin, 5535 Partridge Ct., Harrisburg, PA (US) 17111; Michael F. Verderame, 1882 Sand Hill Rd., Hershey, PA (US) 17033

( * ) Notice: Subject to any disclaimer, the term of this patent is extended or adjusted under 35 U.S.C. 154(b) by 0 days.

(21) Appl. No.: 09/431,843

(22) Filed: Nov. 2, 1999

Related U.S. Application Data

(60) Provisional application No. 60/106,879, filed on Nov. 3, 1998.

(51) Int. Cl.
 C07H 21/04 (2006.01)
 A01N 37/18 (2006.01)
 A61K 38/00 (2006.01)

(52) U.S. Cl. ............... 536/23.5; 514/2; 514/12
(58) Field of Classification Search ............ 435/69.1, 435/70.1, 71.1, 71.2, 252.3, 320.1, 325, 471; 536/23.5; 514/2, 12
 See application file for complete search history.

(56) References Cited

U.S. PATENT DOCUMENTS 5,266,574 A 11/1993 Zagon et al.
5,861,381 A * 1/1999 Chambon et al.

FOREIGN PATENT DOCUMENTS

WO WO 94/01548 A2 * 1/1994

OTHER PUBLICATIONS

Bonaldo MF, et al. Normalization and subtraction: two approaches to facilitate gene discovery. Genome Res. 6(9):701-806, 1996.*
Pellett PE, et al. A strongly immunoreactive virion protein of human herpesvirus 6 variant B strain Z29 identification and characterization of the gene and mapping of a variant-specific monoclonal antibody reactive epitope. Virology 195:521-531, 1993.*
Fliegel L, et al. Molecular cloning of the high affinity calcium-binding protein (Calreticulin) of skeletal muscle sarcoplasmic reticulum. J. Biol. Chem. 264:21522-21528, 1989.*
Everett RD and Fenwick ML. Comparitive DNA sequence analysis of the host shutoff genes of different srains of herpes simplex virus: type 2 strain HG52 encodes a truncated UL41 product J. Gen. Virol. 71:1387-1390, 1990.*
Geisel et al. Accession No. Al115047. Sugano mouse embryo mewa Mus mucsulus cDNA clone, Sep. 1998.*
Hytrek, S. D., et al. (1996) "Identification and characterization of ζ-opioid receptor in human colon cancer", *Am. J. Physiol. 271*:R115-R121.
Zagon, Ian S., et al. (1990) "Demonstration and characterization of zeta (ζ), a growth-related opioid receptor, in a neuroblastoma cell line", *Brain Research 511*: 181-186.
Zagon, Ian S., et al. (1991) "Zeta (ζ), a growth-related opioid receptor in developing rat cerebellum: identification and characterization", *Brain Research 551*: 28-35.
Zagon, Ian S., et al. (1993) "Zeta (ζ), the opioid growth factor receptor: identification and characterization of binding subunits", *Brain Research 605*: 50-56.
Zagon, Ian S., et al. (1989) "Characterization of zeta (ζ) : a new opioid receptor involved in growth", *Brain Research 482*: 297-305.
Zagon, Ian S., et al. (1993) "Production and characterization of polyclonal and monoclonal antibodies to the zeta (ζ) opioid receptor", *Brain Research 630*: 295-302.
Zagon, Ian S., et al. (1987) "Opioid Receptors and Endogenous Opioids in Diverse Human and Animal Cancers [1,2,3]", *JNCI 79(3)*: 1059-1065.
Zagon, Ian S., et al. (1989) "Opioid antagonist modulation of murine neuroblastoma: a profile of cell proliferation and opioid peptides and receptors", *Brain Research 480*: 16-28.
Zagon, Ian S., et al. (1988) "Endogenous Opioids And The Growth Regulation Of A Neural Tumor", *Life Sciences 43*: 1313-1318.

* cited by examiner

*Primary Examiner*—Robert S. Landsman
(74) *Attorney, Agent, or Firm*—Scully, Scott, Murphy and Presser

(57) ABSTRACT

This invention relates to novel nucleic acid molecules coding for opioid growth factor receptors. In particular, the present invention provides isolated nucleic acid molecules coding for human and rat OGF receptors. Antisense molecules, expression vectors and host cells, isolated proteins encoded by such nucleic acid molecules, antibodies directed against such proteins, as well as pharmaceutical compositions derived therefrom are also included. The invention further provides methods of modulating cell growth by using the isolated nucleic acid molecules, the antisense molecules and the antibodies directed against the encoded proteins.

9 Claims, 24 Drawing Sheets
(4 of 24 Drawing Sheet(s) Filed in Color)

Figure 2A

```
1111  -GAGGGGAACAGGCAGGAGGAGCAGGTCCCAGGGGAGGCAGAGATCCCCAGGGTGTCTCTGAGGTAGAGAAAATTGCCCTTAACCTTGAGGAGTGT  400
       GluGlyAsnArgGlnGluGlnValProGlyGluAlaAspProGlnGlyValGluLysIleAlaLeuAsnLeuGluGluCys

1201  -GCCCTTAGCCCTATCAGCCAGGAGACCCAGGGAGGCTGAACCGCCCTGTCCTGTGGCCAGGGTGGCTAATGAGGTAAGAAAGCGGAGGAAG     430
       AlaLeuSerProIleSerGlnGlnGluProArgGluAlaGluProProCysProValAlaArgValAlaAsnGluValArgLysArgArgLys

1291  -GTGGAGGAAGGGCTGAGGGTGATGGAGTAGTAGCAGGCCAGTCAAATGACTAACACTCAAATGATCAGGCCAGTGCCCTCCTACCCCTTCAGAGTGTCCTGAG  460
       ValGluGluGlyAspGlyAspGlyValValSerAsnThrGlnMetGlnAlaSerAsnLeuProProThrProSerGluCysProGlu

1381  -GCCCAAAAGGATGGGAATGGGCCAGAGGACTCAAACAGCCAGTTGGGGCCAGAGGATTCCAAAAGCCAGTGGGCCCGAGGATCCAAAC       490
       AlaGlnLysAspGlyAsnGlyProGluAspSerLysSerGlnValGlyAlaGluAspSerLysSerGlnValGlyProGluAspProAsn

1471  -AGCCAGGTGGGGCTGGAGGACCCCAAACAGCACCCAGGTCGGGCCAGAGGACCCAAACAGCAGCCAGTC                          520
       SerGlnValGlyLeuGluGluAspProAsnSerGlnValGlyProGluAspProAsnSerGlnValGlyProGluAspProAsnSerGlnVal

1561  -GGGCCAGAGGACCCAAACAGCCAGTCGGGCCAGAGGACCCAAACAGCCAGTGTGGGGCCAAGAGCCAAGCTGCCTCTAAGAGCCCTGTG      550
       GlyProGluAspProAsnSerGlnValGlyProGluAspProAsnSerGlnValValGlyProGluGlnAlaAlaSerLysSerProVal

1651  -GAGGACCCTGACTCTGACACTATGGGAACCTCAGTGAGTCAGGAGAGTTGGCAAGGATTGAGGCCTGCTGAACCCCAAAGCCT            580
       GluAspProAspSerAspThrMetGlyThrSerValAspSerGluLeuLeuAlaArgIleGluAlaGluProProLysPro

1741  -TAGAGGTGCATCTCAGTCCTACTCAGCCCACTGCCAGAGGGGTTTCTGAGTCCAGAGCTCTGCCGTAGGCTCTCTTCTTGGTGCCCCACAGTGC
1831  -TGGCCCTCCTCCCTAGTGGTCACTGAGGTGGCCACCAGAGGGACTGAGCCCTGCCCTGCAGGGAAGGCCTTCAGAACCCTCCTTAC
1921  -CTCACTGTGTCCTCCTCCACTGCCCCTGAGCCCTGCGTTGTGATCAGACCCTAAGGGTCTAGAGGGAGGGGCCTCTTCATTAGTCTGGT
2011  -GCCAAGTGAGGCCTTTTCTGAATAAACTCTTTAGACTTTGTCAAAAAAAAAAAAAAAAAAAAAAAAAAAAAAAAAAAAAAAAA
```

Figure 2B

```
  1  GCCGAGCATGGACGACCCCGACTGCGACTCCACCTGGGAGGAGGAGGATGCGGAGGACGGAGGAGGAGGAGGACGAGGAGGACTGCGAGGACGG      90
        MetAspAspProAspCysAspSerThrTrpGluGluGluAspAlaGluAspGlyGluGluAspGluGluAspCysGluAspGly
 29  CGAGGCCCGGCGCGGAGGACGCGGACGCCGCAGGAGGACGACGAGGAGGAGGACGAGGAGGAGTCGGAGGAGCCCGGCGCGGCCCAGTCGTTCCAGTC     180
        GluAlaAlaGlyAlaAlaArgArgAspAlaAspAlaAspAlaAspAlaGlyAspAlaGluGluGlySerGluGluProArgAlaAlaArgProSerPheGlnSer
 59  CAGAATGACAGGGTCCAGAAACTGGCGAGCCACGAGGACACATGTGTAGGTACATATCCGGATCTGGTGAACGAGACTGCAA     270
        ArgMetThrGlySerArgAsnTrpArgAlaThrArgAspMetCysValGlyThrTyrProAspLeuValGluArgAspCysAsn
 89  TGGGGACACGCCAAACTGAGTTTCTACAGAAATGAGATCCGCTTCCTGCCAAGCGTGTTTCATTGAGGACATTCTTCAGAACTGGAC     360
        GlyAspThrProAsnLeuSerPheTyrArgAsnGluIleArgPheLeuProAsnGlyCysPheIleGluAspIleLeuGlnAsnTrpThr
119  GGACAACTATGACCTCCTTGAGGACTTCCTGAGAATCACTCACTCCTACATCCAGTGCTGTTTCCTCGGAGAACCAGGAGTGAACTGGCATGCCAAGCC     450
        AspAsnTyrAspLeuLeuGluAspPheLeuArgIleThrHisSerTyrIleGlnTrpLeuPheProLeuArgGluProGlyValAsnTrpHisAlaLysPro
149  CCTCACGCTCAGGGAGGTCGAGGTGTGTTAAAAGCTCCAGGAGATCCAGGAGATGTCTGTCCGGGCCTACGAGCTCATGCTGGGCTTCTA     540
        LeuThrLeuArgGluValGluValPheLysSerSerGlnLeuIleGlnGluLeuValArgLeuValArgAlaTyrGluLeuMetLeuGlyPheTyr
179  CGGGATCCGGCTGGAGGACACGGGCCGAGCACGAACTACCAGAAGCCTTCCAGAACCTGAACTGGCAGCCA     630
        GlyIleArgLeuGluAspThrArgGlyThrGlyAspArgGlyAlaGlnAsnTyrGlnLysArgPheGlnAsnLeuAsnTrpArgSerHis
209  CAACAACCTCCGCATCACGCATCCTCAAGTCGCCGTGCTGAGCTGAGCTGAGCACTTCCAGGCCCACTGCTCGCTTCTTCCTGGA     720
        AsnAsnLeuArgIleThrArgIleLeuLeuLysSerProCysGluLeuSerLeuGluHisPheGlnAlaProLeuValArgPhePheLeuGlu
239  GGAGACGCTGGTGCGGGAGTGCGGGGAGAGACTGCCCTGGACAGTGCCCTGGACTACTTCATGTTCGCCGTGCTGCGACACCAGCGCCG     810
        GluThrLeuValArgGluArgLeuProGlyValArgLeuArgGlnSerAlaLeuAspTyrPheMetPheAlaValArgCysArgHisGlnArgArg
269  CCAGCTGGTGCACTTCGCCTCGGGAGCACTTCCGGCCCCGCCCCAAGTTCGTCTGGGGCCCCAAGACAAGCTGCCCAAGAGGTTCAAGCCCAG     900
        GlnLeuValHisPheAlaTrpGluHisPheArgProArgCysLysPheValTrpProGlnAspLysLeuArgArgPheLysProSer
299  CTCTCTGCCGCATCCGCTCGGAGGCTCGAGGGCATAGCAAGGTGGGGGGTGGAGGAAGGAAGCCCGGGACCCGACCACGAGGCCCAGCAGCCACCCAGGGTCG     990
        SerLeuProHisProLeuGluLeuGluGlySerArgLysValGluGluGluValGlyArgLysGluGlyAspProAspHisGluAlaSerThrGlnGlyArg
329  GGAGGAGGAGGATGCAGGGGGATGAGCAAGGGGAGGGGCCACGGGGTGGAGCCCCAGGATGCGGGACCCT     1080
        GluGluGluAspAlaGlyAspGluGlnGlyGlyArgValAspGluProArgSerValGluProGlnProArgSerArgAlaGlyProLeu
359  GGAGAGGAGGCAGGGGATGAGGGGGACAGCGGGGGAGAAGATAGGCCCGGGGGAGCCCTAAGCCCAAAGAGACAAGAGAGAGAAGCTGA     1170
        GluArgSerGlnGlyAspGluGlyAspGlnArgGlyGluHisGlyGlyHisGlyGlyGluAspIleArgProLeuSerProLysLysArgLysArgLeuGluGlu
```

```
     GCTGAGCCGGCCGGAGCAGCCGCCCAGAGGGCCAGGCCCTCAGAGTGCCTCAGAGGTGGAGAAGATCGCTCTGAATTTGGAGGGGTGTGG  1260
389  LeuSerArgArgGluGlnProProThrGlyProGlyProGlnSerAlaSerGluValGluLysIleAlaLeuAsnLeuGluGlyCysAla

CCTCAGCCAGGGCAGCCTCAGGACGGGGACCCAGGAAGTGGGCGGTCAGGACCCTGGGGAGGCAGTGCAGCCCTGCCGCCAACCCCTGGG  1350
419  LeuSerGlnGlySerLeuArgThrGlyThrGlnGluValGlyGlyGlnAspProGlyGluAlaValGlnProCysArgGlnProLeuGly

AGCCAGGGTGGCCGACAAGGTGAGGAAGCGGAGGAAGGTGGATGAGGGTACTGGGGACAGTGCTGCGGTGGCCAGTGGTGGTGCCCAGAC  1440
449  AlaArgValAlaAspLysValArgLysArgArgLysValAspGluGlyThrGlyAspSerAlaAlaValAlaSerGlyGlyAlaGlnThr

CTTGGCCCTTGCCGGGTCCCCTGCCCCATCGGGGCACCCCAAGGCTGGACACAGTGAGAACGGGGTTGAGGAGGACACAGAAGGTCGAAC  1530
479  LeuAlaLeuAlaGlySerProAlaProSerGlyHisProLysAlaGlyHisSerGluAsnGlyValGluGluAspThrGluGlyArgThr

GGGCCCAAAGAAGGTACCCCTGGGAGCCCATCGGAGACCCCAGGCCCCAGCCCAGCAGGACCTGCAGGGGACGAGCCAGCCAAGACCCCA  1620
509  GlyProLysGluGlyThrProGlySerProSerGluThrProGlyProSerProAlaGlyProAlaGlyAspGluProAlaLysThrPro

GTCGGAGACCCCAGGCCCCAGCCCGGAGGACCTACAAGGGATGAGCCAGCCCAGGGCCATCGGAGACCCCAGGGCCCCAGCCC        1710
539  SerGluThrProGlyProSerProAlaGlyProThrArgAspGluProAlaGluSerProSerGluThrProGlyProArgProAlaGly

GCAGGGACCTGCAGGGGACGAGCCAGGATCC       1800
569  ProAlaGlyAspGluProAlaGluSerProSerGluThrProGlyProArgProAlaGlyProAlaGlyAspGluProAlaLysIlePro 1890
599  SerGluThrProGlyProSerProAlaGlyProThrArgAspGluProAlaGluSerProSerGluThrProGlyProArgProAlaGly 1980
629  ProAlaGlyAspGluProAlaGluSerProSerGluThrProGlyProArgProAlaGlyProAlaGlyAspGluProAlaGluSerPro 2070
659  SerGluThrProGlyProSerProAlaGlyProThrArgAspGluProAlaLysAlaGlyGluAlaAlaGluLeuGlnAspAlaGluVal 2160
689  GluSerSerAlaLysSerGlyLysPro

CCGGAGCTGCTGCGGGCCCCGTCAGAGCTCGCTTCGTGACCCTTAACCCATGACCCACAGTGCTGCCTCCTGGGCACTATGCA         2250
     GGCATGAGAACCGCGAGGCCCTCAGGAAAGCCCAGGCCTGCAGAAGCCTCCTGGCCTGGCTGTGTCTTCCCCACCCAGCTCTCCCTG    2340
     CGCCCCTGTCTTTGTAAATTGACCCTTCTGGAGTGGGGGCG                                                  2382
```

```
7  SPSETPGPSPAGPAGDEPAESPSETPGPRPA                                              GPAGDEPAESPSETPGPSPAGPTRDEPAE...
4  SPSETPGPSPAGPAGDEPAESPSETPGPRPA                                    GPAGDEPAESPSETPGLRPAGPAGDEPAETPSETPGPSPAGPTRDEPAE...
8  SPSETPGPSPAGPAGDEPAKTPSETPGPSPAGPTRDEPAESPSETPGPRPAGPAGDEPAESPSETPGPRPAGPAGDEPAKSPSETPGPSPAGPTRDEPAE...
                         ↑               ↑               ↑
       1                 2               3               4               5
```

Figure 8E

NUCLEIC ACID MOLECULES ENCODING OPIOID GROWTH FACTOR RECEPTORS

This application claims the priority of U.S. Provisional Application Ser. No. 60/106,879, filed Nov. 3, 1998.

FIELD OF THE INVENTION

This invention relates to novel nucleic acid molecules coding for opioid growth factor receptors. The invention further relates to the use of such nucleic acid molecules and compositions derived therefrom in modulating cell growth.

BACKGROUND OF THE INVENTION

Endogenous opioid peptides, first reported by Hughes and coworkers in 1975 (Hughes et al., *Nature* 258: 577–580, 1975), have been documented to be potent regulators of growth (Zagon and McLaughlin, *Opioid growth factor in the developing nervous system*, in: I. S. Zagon and P. J. McLaughlin (Eds.), *Receptors in the Developing Nervous System*, vol. 1, *Growth Factors and Hormones*, Chapman and Hall, London, UK, 1993, pp. 39–62), as well as neuromodulators (Akil et al., *Ann. Rev. Neurosci.* 7: 223–255, 1984). One native opioid peptide, [Met$^5$]-enkephalin, has been reported to be an inhibitory growth factor in development, cellular renewal, cancer, wound healing, and angiogenesis (Isayama, et al., *Brain Res.* 544: 79–85, 1991; McLaughlin, *Amer. J. Physiol.* 271: R122–129, 1996; Murgo, *J. Natl. Cancer Inst.* 75: 341–344, 1995; Steine-Martin, et al., *Life Sci.* 46: 91–98, 1990; Villiger et al., *EMBO J.* 11: 135–143, 1992; Zagon and McLaughlin, 1993, supra; Zagon et al., *Amer. J. Physiol* 271: R780–R786, 1996; Zagon et al., *Brain Res.* 798: 254–260, 1998; Zagon et al., *Brain Res.* 803: 61–68, 1998. In view of these growth properties, [Met$^5$]-enkephalin has been termed opioid growth factor (OGF) (Zagon and McLaughlin, 1993, supra). OGF is an autocrine produced and secreted peptide that is not cell, tissue, or organ specific. While OGF exhibits activity at physiologically relevant concentrations, it does not elicit physical dependence, tolerance, and/or withdrawal. OGF displays a temporal and spatial distribution consistent with specific growth-related effects and is sensitive to opioid antagonist displacement. OGF has a direct, rapid, prolonged, stereospecific, receptor mediated, non-cytotoxic, and reversible influence on growth both in tissue culture and in prokaryotic and eukaryotic organisms. Blockade of the interaction between endogenous opioids and opioid receptors with compounds such as naltrexone (NTX) enhances growth (McLaughlin et al., *Physiol. Behav.* 62: 501–508, 1997; Zagon, et al., *Science* 221: 671–673, 1983; Zagon et al., *Science* 221: 1179–1180, 1983), suggesting that growth related opioid peptides such as OGF are tonically active. The molecular nature of OGF is well documented, and this peptide is encoded by the preproenkephalin gene (Gubler et al., *Nature* 295: 206–209, 1982; Noda et al. *Nature* 295: 202–206, 1982).

The receptor mediating the action of OGF shares certain pharmacological characteristics of classical opioid receptors, including the binding to opioids, stereospecificity, and naloxone-reversibility (Zagon et al., *Brain Res.* 551: 28–35, 1991; Zagon et al., *Brain Res.* 482: 297–305, 1989). Thus, this receptor was originally—and tentatively—termed the zeta (ζ) opioid receptor. However, physiological, pharmacological, receptor binding assays and immunocytochemical localization experiments have revealed the novel nature of this receptor. In particular, the function (growth), tissue distribution (neural and non-neural), subcellular location (nuclear-associated), transient appearance during ontogeny, ligand specificity ([Met$^5$]-enkephalin), and competitive inhibition profile differ substantially from what is known about classical opioid receptors.

The present invention provides for the first time the molecular information of the receptor for OGF, in particular, the nucleotide and amino acid sequences of such receptor. Comparison of such sequences with those reported for the opioid receptor family shows no structural homology. In view of the pharmacological, biochemical, physiological and molecular differences, the present invention has termed the receptor tentatively identified as the zeta opioid receptor, the OGF receptor (OGFr).

SUMMARY OF THE INVENTION

One embodiment of the present invention is directed to isolated nucleic acid molecules coding for OGF receptors.

In a preferred embodiment, the present invention provides isolated nucleic acid molecules, SEQ ID NOs: 1, 4–5, 7, 9, 11 and 13. Degenerate sequences, splice variant sequences, fragments, sequences having deletions, insertions or substitutions, as well as homologs of SEQ ID NOs: 1, 4–5, 7, 9, 11 and 13 are also contemplated by the present invention.

Another embodiment of the present invention is directed to isolated nucleic acid molecules, the complement sequences of which hybridize under stringent conditions to any of SEQ ID NOs: 1, 4–5, 7, 9, 11 and 13.

In another embodiment, the present invention is directed to antisense nucleotides of any of the above-described nucleic acid molecules, in particular, antisense nucleic acid molecules of SEQ ID NOs: 1, 4–5, 7, 9, 11 and 13. Preferred antisense molecules include SEQ ID NO: 15 and SEQ ID NO: 17, for example.

In still another embodiment, the present invention provides expression vectors in which any of the foregoing nucleic acid molecules or a fragment thereof has been inserted.

In another embodiment, host cells which are transformed with such an expression vector are provided by the present invention.

In still another embodiment, the present invention provides methods of producing recombinant OGFr proteins or peptide fragments thereof by using the nucleic acid molecules of the present invention.

In a further aspect, the present invention provides isolated proteins, the sequences of which are set forth in SEQ ID NOs: 2, 6, 8, 10, 12 and 14. The present invention also contemplates isolated proteins substantially homologous to any of SEQ ID NOs: 2, 6, 8, 10, 12 and 14.

Also embraced by the present invention are functional equivalents or derivatives of any of SEQ ID NO: 2, 6, 8, 10, 12 and 14.

Another embodiment of the present invention is directed to antibodies raised against an OGFr consisting of any one sequence of SEQ ID NOs: 2, 6, 8, 10, 12 and 14, in particular, monoclonal antibodies.

In a further aspect of the present invention, pharmaceutical compositions are provided in which one or more of the isolated nucleic acid molecules, antisense molecules, expression vectors, cells, isolated OGFr proteins or functional derivatives and antibodies directed against OGFr proteins of the present invention, are included.

In one embodiment, the present invention provides a method of detecting the expression of an OGF receptor in a tissue by using a nucleic acid sequence encoding such OGFr or a portion thereof.

In another embodiment, the present invention provides methods for detecting the level of an OGFr in a tissue by using antibodies, particularly, monoclonal antibodies, that specifically recognize the OGFr.

In one embodiment, the present invention provides methods of inhibiting growth of cells in vitro by administering to such cells, an effective amount of nucleic acid molecules coding for an OGFr or a functional derivative thereof.

In another embodiment, the present invention provides methods of promoting growth of cells in vitro by administering to such cells, an effective amount of an OGFr antisense molecule.

In another embodiment, the present invention provides methods of promoting growth of cells in vitro by administering to such cells, an effective amount of an antibody directed against an OGFr thereby interfering or inhibiting the function of the OGFr.

In still another embodiment, the present invention provides methods of treating cancers in a patient by enhancing the function of the OGF ligand-receptor system in the cancerous cells.

Cancers which can be treated by the methods of the present invention include, but are not limited to, cancers of neural tissues such as neuroblastoma, prostate cancer, breast cancer, head and neck cancers, gastrointestinal cancers such as pharyngeal, esophageal, stomach, small and large intestine, liver, rectal, colon and pancreatic, biliary tract cancers including gall bladder and bile duct cancers.

In a preferred embodiment, the present invention provides methods of treating cancers in a patient by administering to such patient, an effective amount of a nucleic acid molecule coding for an OGFr or a functional derivative thereof. More preferably, such methods of the present invention are used to treat cancers which are characterized by a deficiency of OGF receptors on the cancerous cells, for example, pancreatic cancer. Desired nucleic acid molecules can be administered in conjunction with OGF.

In a further embodiment, the present invention provides methods of promoting growth of cells in a subject in need thereof by interfering with the function of the OGF ligand-receptor system.

In a preferred embodiment, the present invention provides methods of promoting growth of cells in a subject in need thereof by administering to such subject, an effective amount of an OGFr antisense molecule or an antibody against OGFr. Such methods can be used in the treatment of wounded tissues, for example.

BRIEF DESCRIPTION OF DRAWINGS

The file of this patent contains at least one drawing executed in color as determined by the U.S. Patent and Trademark Office. Copies of this patent with color drawing(s) will be provided by the Patent and Trademark Office upon request and payment of the necessary fees.

FIGS. 2A–2B depict the nucleotide and amino acid sequences of rat OGFr. 5'- and 3'-untranslated regions are included. Repeats are denoted by single and double underlining.

FIGS. 8A–8B depict the nucleotide sequence (SEQ ID NO: 5) and the predicted amino acid sequence (SEQ ID NO: 6) of human OGFr, clone 8; 5'- and 3'-untranslated regions are included.

FIGS. 8C–8F depict alternatively spliced forms of OGFr. Colors indicate regions of identity between splice variants.

8C. Nucleotide splicing.

8D. Peptide structure of clones 1 and 127 compared to clone 8. Clone 1 and clone 127 lack the imperfect repeats.

8E. Comparison of repeats in clones #4, 7, and 8. Differences in amino acids are noted in red (presumably due to polymorphisms in the population), and repeats are designated by alternate underlining. Repeats are numbered 1–5, and arrows indicate positions of apparent alternative splicing.

Figure 8C:
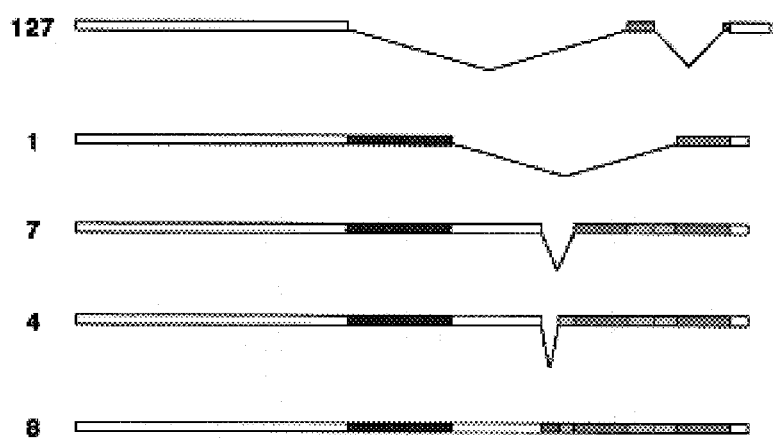
Figure 8D:
Figure 8F:
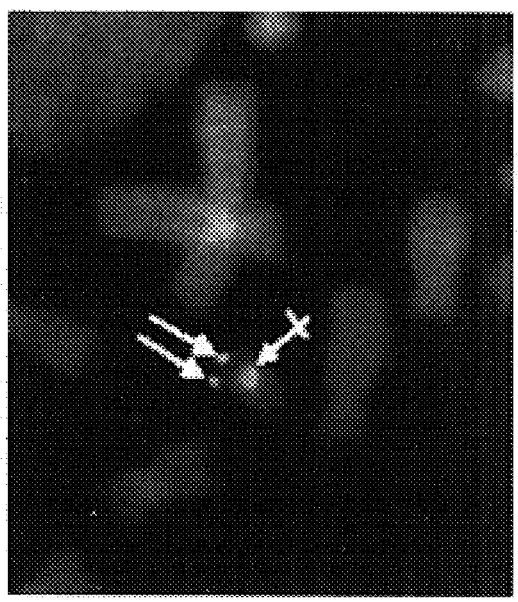
Figure 8F:
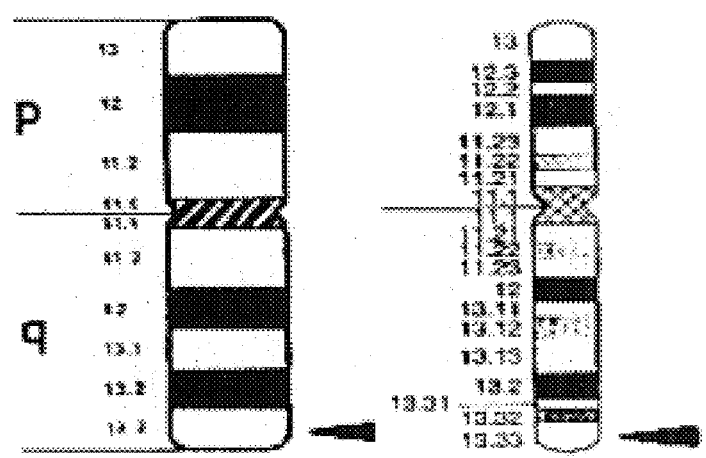
Figure 9A:
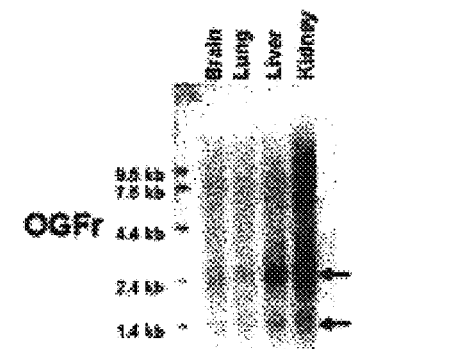
Figure 9B:
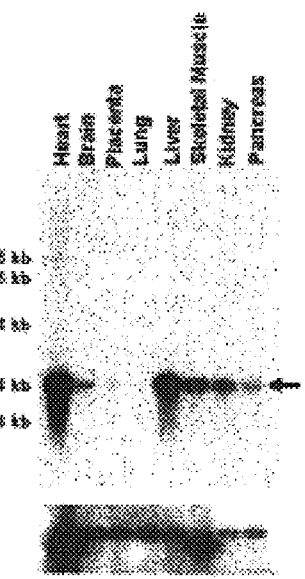
Figure 9C:
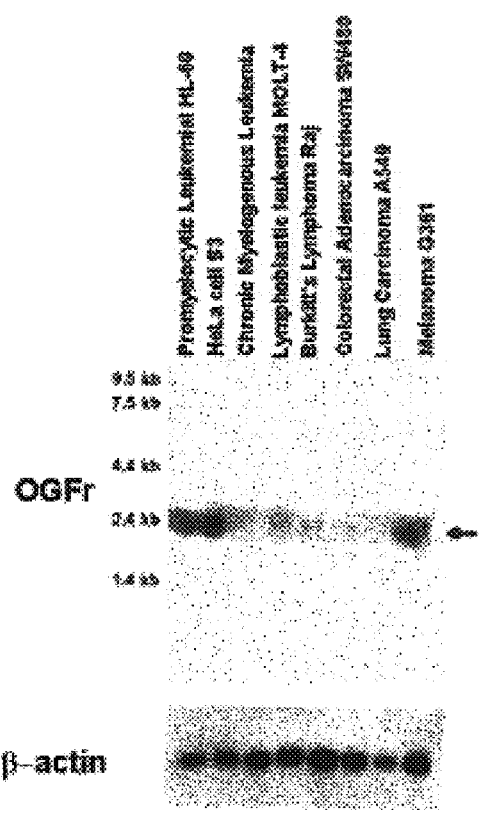
Figure 9D:
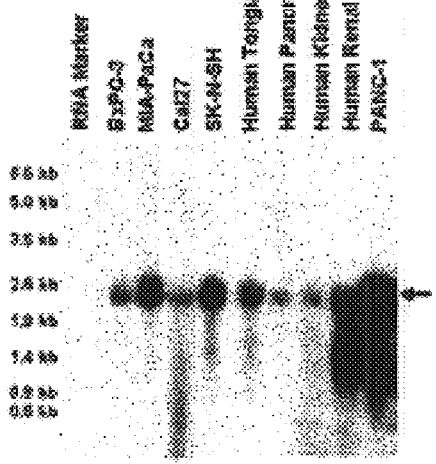

FIG. 8F depicts FISH preparation and a companion ideogram (from the International System for Human Cytogenetic Nomenclature, 1995) showing the localization of OGFr to chromosome 20q13.3 (arrow).

FIGS. 9A–9D depict Northern blot analysis of the receptor for OGF in human fetal (A) and adult (B) tissues, and cancer cells and tissues (C, D); corresponding β-actin level is shown below each blot.

Figure 10:
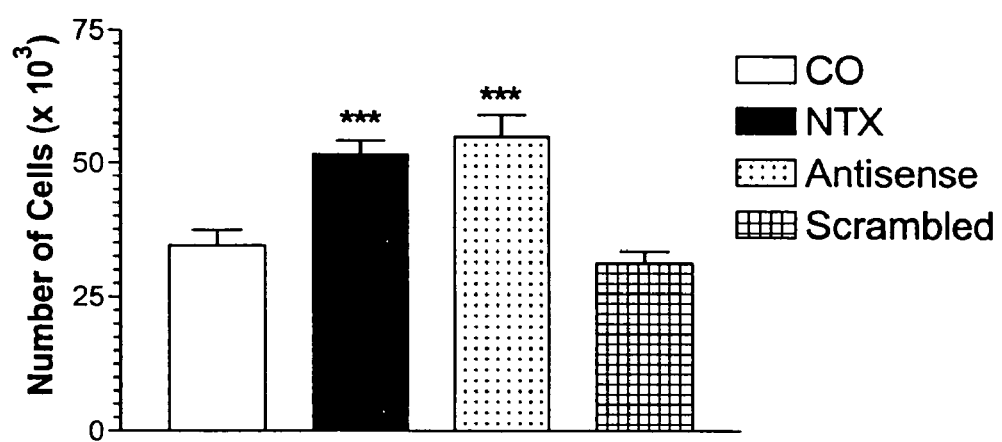

FIG. 10 depicts histogram of cell number in cultures of SK-N-AS human neuroblastoma cells treated for 48 hr with either sterile water (CO), $10^{-6}$ M NTX, $10^{-6}$ M S-ODN, or scrambled oligonucleotide. Cells ($6 \times 10^3$) were plated and compounds and fresh media added 24 hr and 48 hr later. After 72 hr in culture, cells were trypsinized, stained with trypan blue, and counted with a hemacytometer. Significantly different from CO at $p<0.01$ (***).

Figure 11:
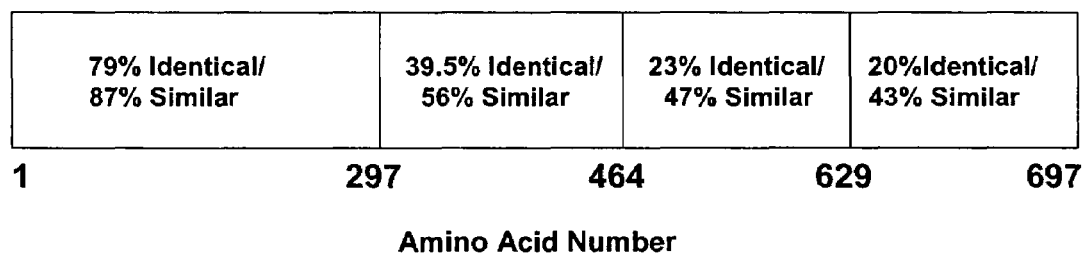

FIG. 11 depicts the comparison of amino acid similarity between human and rat OGFr. The amino acid similarity is not consistent throughout the OGFr, being higher at the N-terminus. Numbers below boxes indicate amino acid position of the boundaries determined by inspection.

Figure 12:
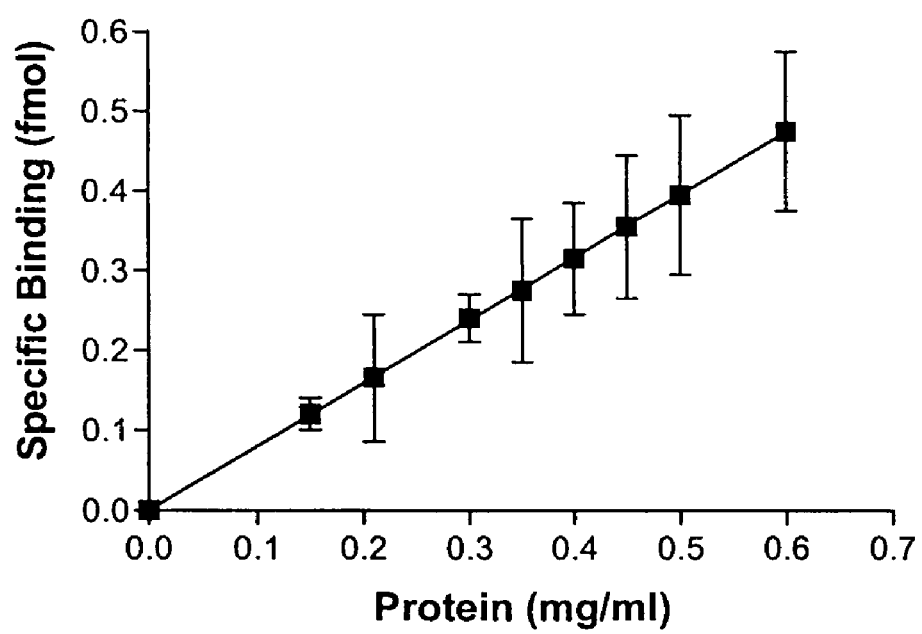

FIG. 12 depicts the dependence of binding of [$^3$H-[Met$^5$]-enkephalin on the protein concentration of PANC-1 nuclear homogenates. Increasing concentrations of protein were incubated with 2 nM radiolabeled [Met$^5$]-enkephalin in the presence or absence of 100 nM unlabeled [Met$^5$]-enkephalin for 60 min at 4° C. at pH 7.4. Values are means±SE for at least 2 experiments performed in duplicate.

Figure 13:
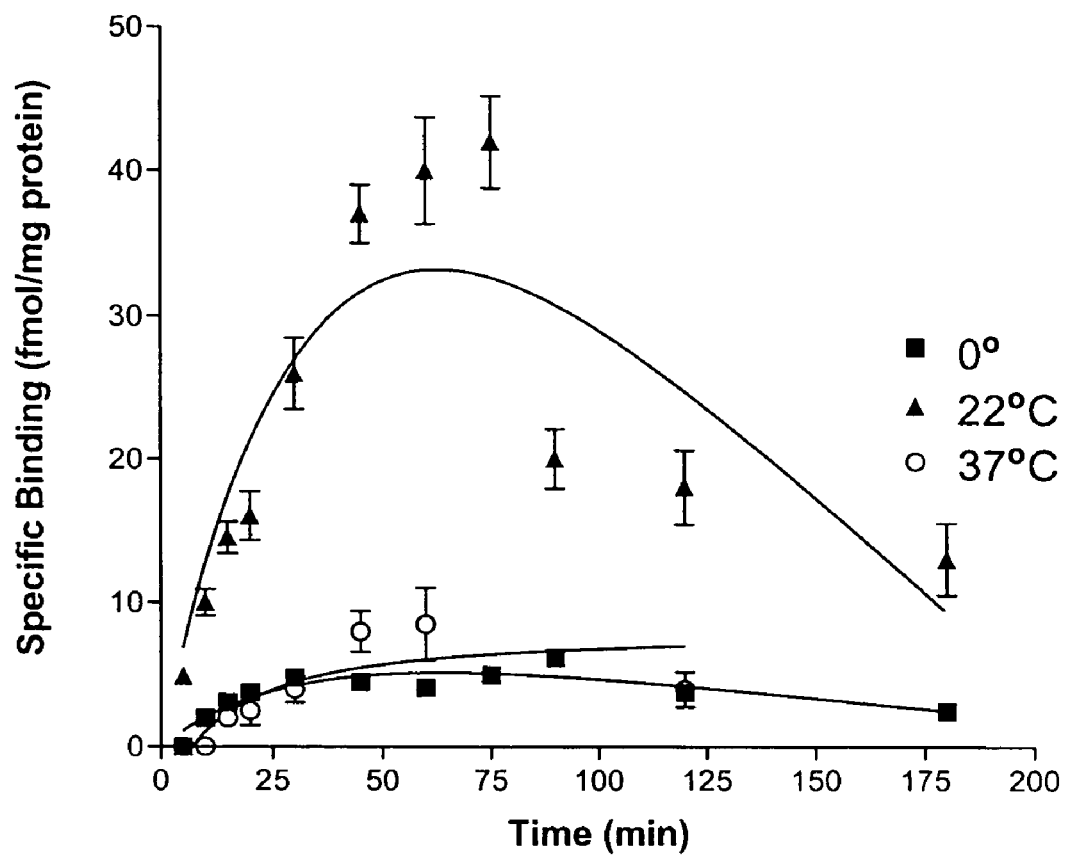

FIG. 13 depicts the dependence of binding of [Met$^5$]-enkephalin to PANC-1 nuclear homogenates on time and temperature of incubation. Nuclear protein homogenates were incubated with 2 nM [$^3$H]-[Met$^5$]-enkephalin in the presence or absence of unlabeled [Met$^5$]-enkephalin (for nonspecific binding) at 4° C., 22° C., or 37° C. for varying periods of time. Data are means±SE for at least 3 experiments performed in duplicate.

Figure 14:
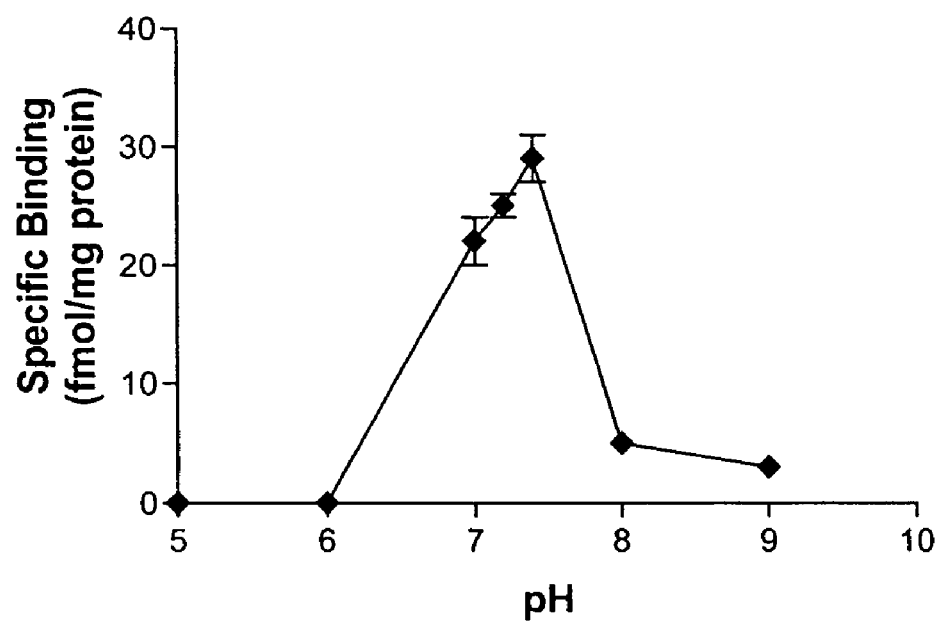

FIG. 14 depicts the dependence of binding of [$^3$H]-[Met$^5$]-enkephalin to PANC-1 nuclear homogenates on pH of the incubation buffer. Nuclear protein homogenates were incubated with 2 nM [$^3$H]-[Met$^5$]-enkephalin in the presence or absence of unlabeled [Met$^5$]-enkephalin (for nonspecific binding) at 22° C. at a variety of pH levels for the buffer. A pH value of 7.4 appeared to be optimal.

Figure 15:
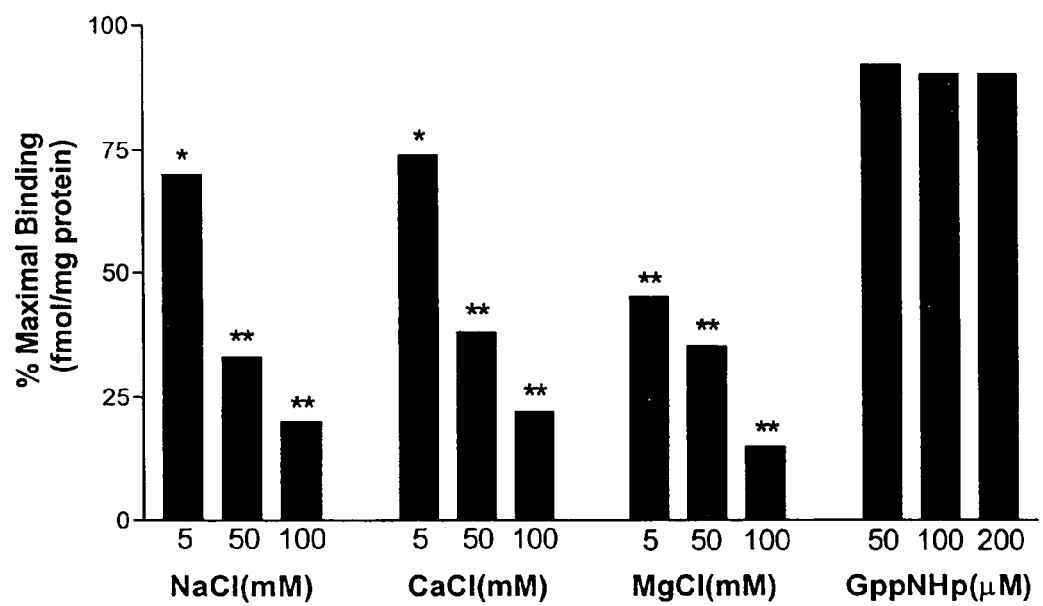

FIG. 15 depicts the effects of cations ($Na^+$, $Ca^{++}$, $Mg^{++}$) and guanylylimidodiphosphate (GppNHp) on binding of [$^3$H]-[Met$^5$]-enkephalin to PANC-1 nuclear homogenates. Histograms represent percentage of maximal binding (mean±SE) obtained using optimal conditions. Significantly different from optimal binding levels at $p<0.05$ (*) or $p<0.01$ (**).

Figure 16A:
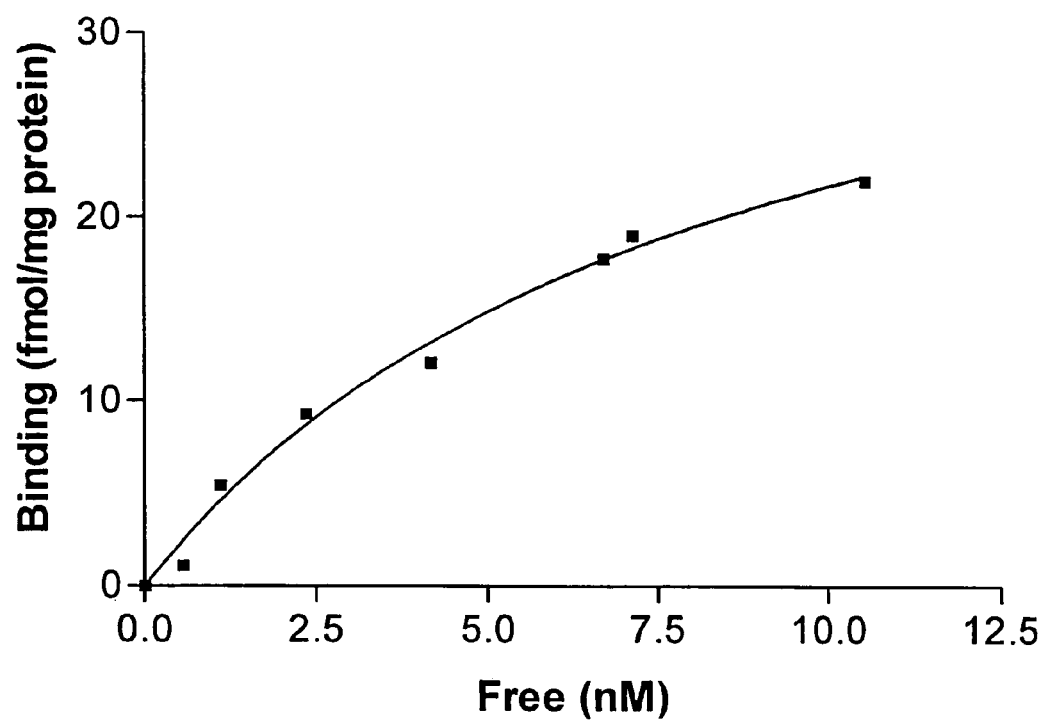
Figure 16B:
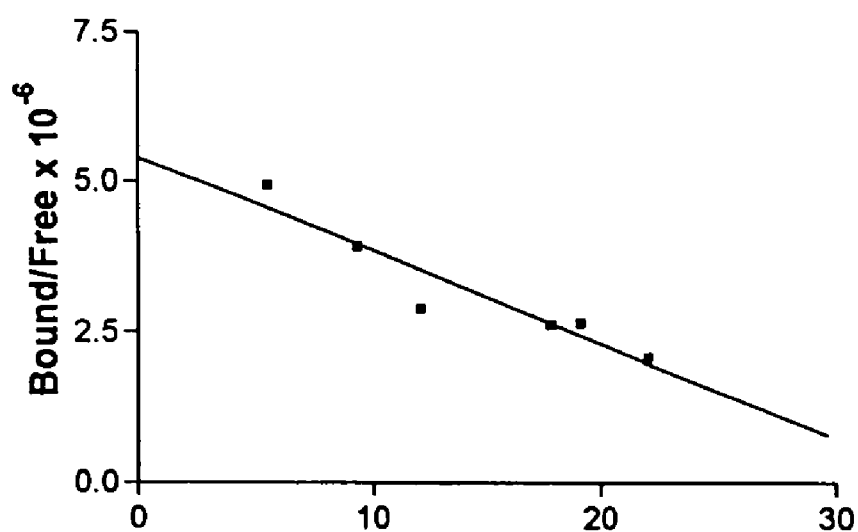

FIGS. 16A–16B depict representative saturation isotherm of specific binding of [$^3$H]-[Met$^5$]-enkephalin to homogenates of PANC-1 nuclear protein. Mean±SE binding affinity ($K_d$) and maximal binding capacity ($B_{max}$) values from 15 assays performed in duplicate. Representative Scatchard plot (inset) of specific binding of radiolabeled [Met$^5$]-enkephalin to PANC-1 protein revealed a one-site model of binding.

DETAILED DESCRIPTION OF THE INVENTION

One embodiment of the present invention is directed to isolated nucleic acid molecules. The nucleic acid molecules of the present invention can be of any mammalian origin, including human, pig, dog, monkey, chicken, cow, horse, sheep, murine, rat and the like.

In particular, the present invention provides isolated nucleic acid molecules coding for OGF receptors.

As used herein, an OGF receptor (OGFr) refers to a protein to which the prototypic ligand OGF binds, and through which the growth-related effects of OGF are mediated. OGF is a tonically suppressive autocrine peptide, and its action on growth as an inhibitory agent is dose-related, reversible, prolonged, independent of serum, and not cytotoxic. The growth-related effects of OGF are associated with cell proliferation, differentiation, and migration, as well as tissue organization. These effects of OGF occur in developing, regeneration, renewing (homeostatsis), wound healing and angiogenesis.

In a preferred embodiment, the present invention provides isolated nucleic acid molecules having SEQ ID NOs: 1, 4–5, 7, 9, 11 and 13.

A cDNA clone having SEQ ID NO: 1 has been isolated from a λgt11 expression cDNA library constructed from fetal rat brain mRNA. Such cDNA encodes a protein of 580 amino acid (SEQ ID NO: 2).

cDNA clones of SEQ ID NOs: 4–5, 7, 9, 11 and 13 encoding multiple alternatively spliced forms of a human OGF receptor have been obtained by assembling the sequences of 5' and 3' RACE products using human placenta mRNA. The longest assembled clone (SEQ ID NO: 5) encodes a protein of 697 amino acids (SEQ ID NO: 6). SEQ ID NOs: 4–5, 7, 9, 11 and 13 share a portion of the nucleotide sequence at the 5' region, but differ in the 3' region. The polypeptide sequences encoded by these cDNA clones are set forth in SEQ ID NOs: 6, 8, 10, 12 and 14. SEQ ID NO: 5 differs from SEQ ID NO: 4 by having additional 118 nucleotides at the 3' untranslated region.

The present invention also contemplates degenerate sequences of SEQ ID NOs: 1, 4, 5, 7, 9, 11 and 13, i.e., nucleic acid molecules encoding any of the polypeptides of SEQ ID NOs: 2, 6, 8, 10, 12 and 14, which employ alternative codons to those present in SEQ ID NOs: 1, 4–5, 7, 9, 11 and 13.

Fragments of SEQ ID NOs: 1, 4–5, 7, 9, 11 and 13 are also provided by the present invention, for example, SEQ ID NO: 3 (a partial rat cDNA clone).

As used herein, "a fragment of a nucleic acid molecule" should be at least about 12, preferably about 15 bp in length. Fragments of SEQ ID NOs: 1, 4–5, 7, 9, 11 and 13 can be used as probes to screen cDNA libraries for OGFr genes from other species using, e.g., Southern Blot or PCR. Fragments of SEQ ID NOs: 1, 4–5, 7, 9, 11 and 13 can also be inserted in expression vectors to make the encoded peptides.

In another embodiment, the present invention is directed to nucleic acid molecules that are substantially homologous to any of SEQ ID NOs: 1, 4–5, 7, 9, 11 and 13.

The phrase "substantially homologous" when referring to nucleotide sequences, denotes the degree of homology of at least 45%, more preferably, at least about 60%, even more preferably, at least about 75%. The degree of homology as used herein is calculated by using the GAP program with a unary comparison matrix, a 3.0 gap penalty, an additional 0.10 penalty for each symbol in each gap, and no penalty for end gaps.

Nucleic acid molecules substantially homologous to any of SEQ ID NOs: 1, 4–5, 7, 9, 11 and 13 can be obtained by a variety of well-known techniques. For example, oligonucleotides or DNA fragments can be made from SEQ ID NOs: 1, 4–5, 7, 9, 11 and 13 and employed to screen cDNA libraries for homologous nucleic acid molecules using techniques such as PCR or DNA hybridizations under stringent conditions.

"Stringent conditions" as used herein refer to conditions such as, 18 hours of hybridization at 65°, followed by four one-hour washes with 2× SSC, 0.1% SDS, and a final wash with 0.2× SSC, more preferably 0.1× SSC, and 0.1% SDS for 30 minutes, as well as alternate conditions which afford the same level of stringency, and more stringent conditions.

Thus, isolated nucleic acid molecules, the complement sequences of which hybridize under stringent conditions to any of SEQ ID NOs: 1, 4–5, 7, 9, 11 and 13, are also included in the present invention.

Nucleic acid molecules that are substantially homologous to the subject nucleic acid molecules or hybridize to the complement sequences of the subject nucleic acid molecules, also include variants of the subject nucleic acid molecules, such as alternative spliced forms and degenerate forms.

Given the nucleic acid molecules encoding OGF receptors, those skilled in the art can readily make modifications, including substitutions, deletions or additions of one or more base pairs, to obtain nucleic acid molecules coding for modified forms of opioid receptors. For example, those skilled in the art can identify the domain(s) that are responsible for the binding of OGF and the domain(s) that interacts with downstream signaling molecules, and thus can make modified forms of OGF receptors that either have superior OGF binding capacities, or can bind OGF but can not interact with downstream signaling molecules so as to accomplish the desired OGF-mediated biological function. Modified OGF receptors can be in the form of substitutions, deletions (including truncations) or insertions of one or more amino acids. Depending on the circumstance, modified forms of OGF receptors can be used to modulate cell growth, either to stimulate or to inhibit cell growth.

In another embodiment, the present invention is directed to antisense nucleotides of any of the above-described nucleic acid molecules, in particular, antisense nucleic acid molecules of SEQ ID NOs: 1, 4–5, 7, 9, 11 and 13.

In a preferred embodiment, the present invention provides antisense molecules SEQ ID NO: 15 and and SEQ ID NO: 17.

As used herein, the term "antisense nucleotide", "antisense oligonucleotide" or "antisense molecule" refers to an oligonucleotide that hybridizes under physiological conditions to a particular gene or to an mRNA transcript of such gene and, thereby, inhibits the transcription of such gene and/or the translation of such mRNA. The antisense molecules are designed so as to interfere with transcription or translation of a target gene upon hybridization with the target gene or its mRNA.

It is recognized by those skilled in the art that the exact length of the antisense oligonucleotide and its degree of complementarity with its target depend upon the specific target selected. Preferably, an antisense oligonucleotide is constructed so as to bind selectively with the target under physiological conditions, i.e., to hybridize substantially more to the target sequence than to any other sequence in the target cell under physiological conditions.

Based upon SEQ ID NOs: 1, 4–5, 7, 9, 11 and 13, those skilled in the art can generate appropriate antisense molecules for use in accordance with the present invention. In general, such antisense oligonucleotides should be at least 7, and preferably, at least about 15 consecutive bases which are complementary to the target DNA or mRNA. Most preferably, the antisense oligonucleotides contain a complementary sequence of 20–30 bases. Although oligonucleotides may be designed according to any region of a gene or its mRNA transcript, preferably, the antisense oligonucleotides are complementary to the 5' region or upstream sites such as translation initiation, transcription initiation or promoter sites.

The antisense oligonucleotides of the invention can be composed of "natural" deoxyribonucleotides, ribonucleotides, or any combination thereof, which are covalently linked, as in natural systems, via a phosphodiester internucleoside linkage.

The antisense oligonucleotides of the invention also may include "modified" oligonucleotides. The term "modified oligonucleotide" as used herein refers to an oligonucleotide in which a synthetic linkage other than a natural 5'–3' phosphodiester linkage is present, and/or a modified base or chemical group is present. Synthetic internucleoside linkages include phosphorothioates, alkylphosphonates, phosphorodithioates, phosphate esters, alkylphosphonothioates, phosphoramidates, carbamates, carbonates, phosphate triesters, acetamidates, peptides, and carboxymethyl esters. Modified oligonucleotides can include a 2'-O-alkylated ribose group, sugars such as arabinose instead of ribose, base analogs such as C-5 propyne modified bases (Wagner et al., *Nature Biotechnology* 14:840–844, 1996).

In another embodiment, the present invention provides expression vectors in which any of the foregoing nucleic acid molecules or a fragment thereof has been inserted for purposes of propagation of such nucleic acid molecule and/or production of the polypeptide encoded thereby.

For propagation of a desired nucleic acid molecule, the nucleic acid molecule can be inserted into a vector having a replication origin operable in a desired host, and preferably, a selectable marker, e.g., a marker conferring resistance to an antibiotic. Many of these vectors are available to those skilled in the art, such as pBR322 (New England Biolab), pBluescript (Strategene) and the like. For purpose of expression, a desired nucleic acid molecule can be placed in an operable linkage to a promoter and inserted into a vector appropriate for directing expression in a desired host. For expression in a eukaryotic cell, viral vectors are preferred, e.g., a retroviral, adenoviral, herpes simplex viral vectors or yeast vectors. For expression in a prokaryotic cell, phage vectors are preferred. For expression in an insect cell, baculovirus-based vectors can be used.

In still another embodiment, host cells which are transformed with such an expression vector are provided by the present invention. Those skilled in the art are equally familiar with the choice of cell lines and the procedures to transform such cell lines. Examples of the cell lines include, but are not limited to, eukaryotic cells, e.g., COS cells such as COS-7, CHO cells such as CHO-1, NIH 3T3 cells, yeast cells such as strains of *Saccharomyces* and *Pichia pastoris*, insect cells such as *Spodoptera frugiperda*; and prokaryotic cells, e.g., strains of *E. coli*, strains of *Pseudomonas* such as *Pseudomonas aeruginosa* or strains of *Bacillus*.

In another embodiment, the present invention provides methods of producing recombinant OGFr proteins or peptide fragments thereof by using the nucleic acid molecules of the present invention.

In accordance with such methods, a nucleic acid molecule encoding an OGFr or a peptide fragment thereof is inserted into an expression vector, which is then transformed into a desired host cell. Choices of expression vectors and host cells have been described herein above. Recombinantly expressed proteins can be purified from the transformed cells following routine procedures.

In a further aspect, the present invention provides isolated proteins, the sequences of which are set forth in SEQ ID NOs: 2, 6, 8, 10, 12 and 14.

According to the present invention, SEQ ID NO: 2 sets forth the amino acid composition of rat OGFr, SEQ ID NO: 6, 8, 10, 12 and 14 set forth the amino acid compositions of 5 alternatively spliced human OGFr, with SEQ ID NO: 6 constituting the longest polypeptide (697 aa).

The present invention also contemplates isolated proteins substantially homologous to any of SEQ ID NOs: 2, 6, 8, 10, 12 and 14. Such homologous proteins can be of any mammalian origin which includes human, pig, dog, monkey, chicken, cow, horse, sheep, murine, rat and the like.

By "substantial homologous" is meant the degree of amino acid similarity of at least about 45%, preferably at least about 60%, and more preferably at least about 75%. As used herein, the degree of similarity is calculated using the BESTFIT Program (Wisconsin GCG release 8) with the following set of parameters: Gap Weight=5.0, Length Weight=0.3, Average Match=1.0, and Average Mismatch=0.9.

Also embraced in the present invention are functional equivalents or derivatives of any of SEQ ID NO: 2, 6, 8, 10, 12 and 14.

For purpose of the present invention, "a functional derivative of a protein" includes any modified form of such protein which retains one or more of the biological activities of such protein. A typical biological activity of an OGFr is its specific binding to $Met^5$-enkephalin, which binding can be reversibly blocked by naltrexone or naloxone. Other biological activities of an OGFr manifest as, e.g, inhibition of cell growth.

The modification of an OGFr can include amino acid deletions, insertions, substitutions or truncations. It is appreciated by those skilled in the art that regions of OGFrs that are well conserved among species may be critical in preserving the biological activities of the OGFrs. Notably in this regard, a prominent feature shared by the isolated proteins of the present invention is the presence of multiple copies of imperfect repeats, as indicated in FIGS. 2A–2B and FIGS. 8A–8F. In addition, when comparing SEQ ID NO: 2 (rat OGFr) with SEQ ID NO: 6 (human OGFr) (FIG. 11), a striking similarity is observed in the first 297 amino acids, with 87% being similar and 79% identical. Beyond this point, the number of both similar and identical amino acids drops notably. Thus, a 56% similarity and a 40% identical amino acid profile could be found from amino acids 297 to 464; a similarity ranging from 43 to 47%, and identical amino acids ranging from 20 to 23% were found thereafter. Therefore, rat OGFr and human OGFr have a great similarity at the N terminus, but dissimilarities at the C terminus.

Another embodiment of the present invention is directed to antibodies raised against an OGFr consisting of any one sequence of SEQ ID NOs: 2, 6, 8, 10, 12 and 14.

The antibodies of the present invention can be generated by using a full-length OGFr protein or a portion thereof as an immunogen. For the purpose of raising antibodies, "a portion of an OGFr protein" refers to a peptide of at least 8 or 9 amino acids. Preferably, the protein or a portion thereof for use as an antigen, is obtained from a recombinant expression system, or chemical synthesis in a standard peptide synthesizer.

Antibodies can be generated by injecting an effective amount of an OGFr protein or a portion thereof into a suitable animal, alone or in combination with an adjuvant. Such animal can include rabbit, chicken, rat, mouse, goat, horse and the like. Both polyclonal antibodies and monoclonal antibodies are contemplated by the present invention. The procedures for making polyclonal and monoclonal antibodies are well known in the art and can be found in, e.g., Harlow, E. and Lane, D., *Antibodies: A Laboratory Manual*, Cold Spring Harbor Press, 1988.

In a further aspect of the present invention, pharmaceutical compositions are provided in which one or more of the isolated nucleic acid molecules, antisense molecules, expression vectors, cells, isolated OGFr proteins or functional derivatives and antibodies directed against OGFr proteins of the present invention, are included.

The pharmaceutical compositions of the present invention can also include a pharmaceutically-acceptable carrier. As used herein, "a pharmaceutically-acceptable carrier" includes any and all solvents, dispersion media, isotonic agents and the like. Except insofar as any conventional media, agent, diluent or carrier is detrimental to the recipient or to the therapeutic effectiveness of the active ingredients contained therein, its use in practicing the methods of the present invention is appropriate. The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof. The carrier for use in the present methods can also be a controlled release matrix, a material which allows the slow release of substances mixed or admixed therein. Examples of such controlled release matrix material include, but are not limited to, sustained release biodegradable formulations described in U.S. Pat. No. 4,849,141 to Fujioka et al., U.S. Pat. No. 4,774,091 to Yamashira, U.S. Pat. No. 4,703,108 to Silver et al., and Brem et al. (*J. Neurosurg.* 74: 441–446, 1991), all of which are incorporated herein by reference.

The pharmaceutical compositions of the present invention can also include other appropriate active ingredients, such as pentapeptide $Met^5$-enkephalin.

In accordance with the present invention, the active ingredients of the present pharmaceutical compositions can be combined with the carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. When appropriate, the pharmaceutical compositions of the present invention should be made sterile by well known procedures. For example, solutions can be made sterile by filter sterilization or autoclave. To obtain a sterile powder, sterilized solutions can be vacuum-dried or freeze-dried as necessary.

In a further aspect of the invention, the nucleic acid molecules encoding an OGFr or a portion thereof, as well as the antibodies against an OGFr, are employed to detect the level or the expression of an OGFr in a tissue or organ. Comparison of the level or the expression of an OGFr within healthy and unhealthy tissues, permit detection of an abnormality of the level or the expression of such OGFr.

In one embodiment, the present invention provides a method of detecting the expression of an OGF receptor in a tissue of a subject by using a nucleic acid sequence encoding the OGFr or a portion thereof.

In general, total RNA can be isolated from a tissue sample of the subject. The level of the OGFr mRNA can be analyzed in various assays, such as Northern Blot Analysis or reverse transcriptase-coupled PCR analysis. The nucleotide sequence for use in these assays should be at least about 15 or 16 base pairs in length. The nucleotide reagent of the present invention can be detectably labeled, for example, with a radioisotope, a fluorescent compound, or a chemiluminescent compound. The teachings for any of the above-described procedures are well-known to those skilled in the art and can be found in, e.g., *Current Protocols in Molecular Cloning* (Ausubel et al., eds., John Wiley & Sons, New York).

In another embodiment, the present invention provides methods for detecting the level of an OGFr in a tissue by using antibodies, particularly, monoclonal antibodies, that specifically recognize the OGFr.

According to the present invention, the level of an OGFr in a tissue can be determined using an antibody and a variety of in vitro assays. Generally, a tissue sample can be taken from the subject, and depending on the assay used, the sample may need to be pretreated. For example, cells can be homogenized, proteins can be extracted from the homogenized cells.

The in vitro assays which can be employed herein include, e.g., immunoassays that are based on antigen capture, antibody capture (e.g., ELISA, Western Blot, etc), or two antibody sandwich assay (either forward or reverse mode). Multiple teachings are available for those skilled in the art. See, e.g., Harlow, E. and Lane, D., *Antibodies: A Laboratory Manual*, Cold Spring Harbor Press, 1988.

The antibodies or the proteins isolated from the sample can be utilized in liquid phase or bound to a solid phase carrier. Examples of well-known carriers include glass, polystyrene, polypropylene, polyethylene, dextran, nylon, amylases, natural and modified cellulose, polyacrylamides, agaroses and magnetite. In addition, the antibodies or the proteins isolated from the tissue sample can be detectably labeled in various ways for a quantitative determination. Examples of detectable labels include secondary antibodies, enzymes such as horseradish peroxidase, β-galactosidase or alkaline phosphatase, fluorophores or radioisotope.

In accordance with the present invention, antibodies can also be used in vivo for detecting the level of an OGFr in a subject. Monoclonal antibodies are preferred for in vivo detection.

In using a monoclonal antibody for in vivo detection, the monoclonal antibody is detectably labeled, e.g., with a radioisotope. The skilled artisan can chose a radioisotope according to the type of detection instrument that is available. The chosen radioisotope should have a type of decay which is detectable for a given type of instrument. Preferably, the chosen radioisotope has a half life that is long enough for detection at the time of maximum uptake by the subject, but short enough to minimize deleterious radiation to the subject. A radioisotope suitable for in vivo imaging methods of the present invention does not have a particle emission, but produces a large number of photons in the 140–250 keV range which may be readily detected by conventional gamma cameras.

According to the present invention, radioisotopes may be coupled to immunoglobulin by using an intermediate functional group, particularly for binding metallic ion-type of radioisotopes to immunoglobulins. Appropriate intermediate functional groups include the bifunctional chelating agents such as diethylenetriaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{88}$Zr, and $^{201}$Tl.

A monoclonal antibody suitable for use in the present methods can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

In accordance with the present invention, a labeled monoclonal antibody can be administered in any appropriate manner, such as via an oral, ophthalmic, nasal, transdermal, parenteral (e.g., intravenous, intraperitoneal, intradermal, subcutaneous or intramuscular), intratumor, intraembryonic, or intrafetal route, to the subject of interest in a quantity that is sufficient to enable a specific detection of the OGFr, and that allows rapidly clearance of the reagent from the subject in order to give the best target-to-background signal ratio. The dosage of detectably labeled monoclonal antibody can vary depending on such factors as age, gender, and severity of the disorder of the subject, or the subject's response to a therapeutic regimen. Those skilled in the art can determine the appropriate dose of a monoclonal antibody reagent using conventional techniques. As a general rule, the dosage of a monoclonal antibody can fall in the range of about 0.001 mg/m$^2$ to about 500 mg/m$^2$, preferably 0.1 mg/m$^2$ to about 200 mg/m$^2$, most preferably about 0.1 mg/m$^2$ to about 10 mg/m$^2$. In vivo imaging techniques are described in U.S. Pat. No. 4,036,945 and U.S. Pat. No. 4,311,688, the disclosures of which are incorporated herein by reference.

In a further aspect of the present invention, the nucleic acid molecules encoding an OGFr or functional derivatives thereof or modified forms thereof, the antisense molecules and antibodies directed against an OGF, are employed to modulate cell growth.

An OGF receptor protein acts together with its native ligand, opioid peptide [Met$^5$]-enkephalin (or OGF), to inhibit cell growth. According to the present invention, such ligand-receptor signaling system can be manipulated to achieve desired effects under various physiological circumstances. For example, in cases of cancer, it is desirable to enhance or potentiate the activity of the OGF ligand-receptor signaling system in cancerous cells thereby inhibiting the growth of the cancerous cells. On the other hand, in cases of cellular renewal or regeneration, wound healing or angiogenesis, for example, it maybe desirable to inhibit or reduce the activity of the OGF ligand-receptor signaling system in cells of the desired tissues, thereby enhancing or accelerating the growth of such cells. Thus, the term "modulating" as used herein refers to regulating and manipulating to enhance or reduce the activity of the OGF ligand-receptor signaling system.

In one embodiment, the present invention provides methods of inhibiting growth of cells in vitro in need of such inhibition by introducing to such cells in vitro, an effective amount of nucleic acid molecules coding for an OGFr or a functional derivative thereof. The nucleic acid molecules can be introduced to such cells by well-known procedures, e.g., transfection. Such nucleic acid molecules can be introduced to the cells in conjunction with Met$^5$-enkephalin.

In another embodiment, the present invention provides methods of promoting growth of cells in vitro in need of such promotion by introducing to such cells, an effective amount of an OGFr antisense molecule. The antisense molecules can be introduced to the cells by, e.g., simply adding such antisense molecules to the culture media of the cells.

In another embodiment, the present invention provides methods of promoting growth of cells in vitro in need of such promotion by introducing to such cells, an effective amount of an antibody directed against an OGFr thereby interfering or inhibiting the function of the OGFr. The antibodies can be introduced to the cells by, e.g., simply adding such antibody to the culture media of the cells.

In still another embodiment, the present invention provides methods of treating cancers in a patient by enhancing the function of the OGF ligand-receptor system in the cancerous cells.

In a preferred embodiment, the function of the OGF ligand-receptor system in the cancerous cells can be enhanced by providing the cancerous cells additional nucleic acid molecules encoding OGF receptors.

Thus, the present invention provides methods of treating cancers in a patient by administering to such patient, an effective amount of nucleic acid molecules coding for an OGFr or a functional derivative thereof.

For the purposes of the present invention, the term "treating" means preventing the onset of cancer, inhibiting the growth of existing cancer, preventing the recurrence of cancer, or arresting cancer completely.

Cancers which can be treated by the methods of the present invention include, but are not limited to, cancers of neural tissues such as neuroblastoma, prostate cancer, breast cancer, head and neck cancers, gastrointestinal cancers such as pharyngeal, esophageal, stomach, small and large intestine, liver, rectal, colon and pancreatic, biliary tract cancers including gall bladder and bile duct cancers.

More preferably, the methods of the present invention are used to treat cancers which are characterized by a deficiency of OGF receptors on the cancerous cells. According to the present invention, an example of such cancer is pancreatic cancer.

A deficiency of OGF receptors can be due to insufficient expression of the receptors or expression of non-functional receptors, as compared with controls, e.g., adjacent normal cells from the same individual or cells from pooled normal individuals.

A variety of assays can be used to determine whether there is a deficiency of OGF receptors in subject cells. Such assays include those described herein above for detecting the level or the expression of OGFr receptors, e.g., Northern Blot or RT-PCR using nucleic acid molecules, and immunoassays using antibodies. Other assays include binding assays which determine the Met$^5$-enkephalin binding capacity of subject cells or protein extracted therefrom. Examples of such binding assays are provided hereinafter (Example 6).

Preferably, a nucleotide sequence encoding an OGF or a functional derivative thereof for use in treating cancers is provided in an expression vector, e.g., a typical gene therapy vector. Preferred gene therapy vectors include retroviral, adenoviral, herpes simplex viral, adeno-associated viral and vaccinia vectors. Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. More preferably, a non-human primate retroviral vector is employed, such as the gibbon ape leukemia virus (GaLV), thereby providing a broader host range than murine vectors, for example. Gene therapy vectors can be made tissue specific by, for example, linking the nucleotide sequence to a tissue-specific promoter. Multiple teachings of gene therapy are available for those skilled in the art, e.g., W. F. Anderson (1984) "Prospects for Human Gene Therapy" *Science* 226: 401–409; S. H. Hughes (1988) "Introduction" *Current Communications in Molecular Biology* 71: 1–12; N. Muzyczka and S. McLaughlin (1988) "Use of Adeno-associated Virus as a Mammalian Transduction Vector" *Communications in Molecular Biology* 70: 39–44; T. Friedman (1989) "Progress Toward Human Gene Therapy" *Science* 244: 1275–1281 and W. F. Anderson (1992) "Human Gene Therapy" *Science* 256: 608–613.

The amount of a nucleic acid molecule to be therapeutically effective can be determined according to the age and the condition of the subject.

Desired nucleic acid molecules can be administered in conjunction with OGF. Other appropriate materials, such as pharmaceutical carriers, can be administered together with the nucleic acid molecules as well. Any of the foregoing described pharmaceutically acceptable carriers can be used, and can be admixed with the nucleic acid molecules in the manner described hereinabove.

The administration of the desired nucleic acid molecules, either alone or with other appropriate material, may be carried out in any convenient manner, including by aerosol inhalation, injection, ingestion, transfusion, implantation or transplantation. Preferably, the administration is carried out by injection, including subcutaneous, intradermal, intramuscular, transdermal, intraperitoneal (i.p.), intra-arterial (i.a.), intravenous (i.v.) injection, or direct injection into the tumor. Multiple administrations may be required, which can be determined by a physician.

In a further embodiment, the present invention provides methods of promoting growth of cells in a subject in need thereof by interfering with the function of the OGF ligand-receptor system.

According to the present invention, the function of the OGF ligand-receptor system can be inhibited by using antisense molecules which interfere with the expression of OGF receptors, or by using antibodies against OGF receptors which interfere, via steric hindrance, e.g., with the function of OGF receptors.

Accordingly, In a preferred embodiment, the present invention provides methods of promoting growth of cells in a subject in need thereof by administering to such subject, an effective amount of an OGFr antisense molecule or an antibody against OGFr.

Such methods of the present invention can be used to assist in the healing of wounded tissues or organs, including but not limited to the skin, the cornea, liver, uterus, nerves, subcutaneous tissues, mucosal tissues, intestinal tissues, and fetal tissues.

Antisense molecules for use in the methods of the present invention can be placed on expression vectors, such as gene therapy vectors described hereinabove.

The amount of an antisense molecule or an antibody to be therapeutically effective can be determined according to the age and the condition of the subject.

Both antisense molecules and antibodies can be administered alone or in combination with one or more pharmaceutically-acceptable carriers. Such carriers have been described hereinabove. Antisense molecules or antibodies can be admixed with one or more carriers in manners described hereinabove, and then administered via any of the foregoing routes.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

EXAMPLE 1

Isolation of a cDNA Clone Encoding a Rat OGF Binding Protein

An antibody against the rat OGF binding protein (BO461) was produced according to published procedures (Zagon et al., Brain Res. 630: 295–302, 1993). In brief, 2-dimensional gels of the nuclear fraction (P1) from a 6-day old rat cerebellum were transferred to nitrocellulose, and ligand blotting with [$^{125}$I]-[Met$^5$]-enkephalin was performed to identify an OGF binding protein (Zagon et al., Brain Res. 482: 297–305, 1989). The protein was electroeluted and injected into New Zealand white rabbits to generate polyclonal antibodies. Serum was collected and purified using ammonium sulfate precipitation and DEAE Affi-blue gel filtration.

One million plaques from a λgt11 expression cDNA library (oligo-dT primed, original complexity of $1.6 \times 10^6$ pfu with insert sizes ranging from 0.6 to 4.0 kb), constructed from 18-day old fetal rat brain mRNA (Clontech, Palo Alto, Calif.), were screened using the polyclonal antibody that recognized the OGF binding protein. Immunoreactive plaques were identified by reaction with horseradish peroxidase or [$^{125}$I]-protein A. Thirty-two plaques reacted positively to the BO461 antiserum, of which four were purified and subjected to restriction digestion. One of these plaques, designated clone #14 (SEQ ID NO: 3), was characterized further.

Figure 1:
FIG. 1 depicts tissue distribution of mRNA detected by the cDNA clone of OGFr. Total RNA was isolated from 6-day cerebellum and brain and from adult cerebellum (25 mg/lane) and separated on a 1.2% agarose gel containing 6% formaldehyde and transferred to a nylon membrane and hybridized with [$^{32}$P]-dCTP labeled cDNA clone #14. A single 2.1 kb mRNA was detected in all tissues examined. The Northern was stripped and hybridized with [$^{32}$P]-dCTP labeled G3PDH, a constitutively expressed mRNA, to demonstrate equal loading of the RNA samples.

The 1000 bp cDNA insert from clone #14 was labeled with [$^{32}$P]dCTP and used to probe Northern blots of total RNA isolated from 6-day old and adult rat cerebellum. Northern blot analysis was performed according to McLaughlin and Allar (Mol. Brain Res. 60: 160–167, 1998). In brief, RNA was isolated from 6-day old and adult rat tissues. Membranes were hybridized at 42° C. for 16–18 hr in fresh prehybridization buffer containing $10^6$ cpm/ml of random prime labeled clone #14 cDNA. Filters were subjected to final washes at 60° C. with 0.1× SSC containing 0.1% SDS for 30 min, wrapped in plastic while wet, and exposed to autoradiography film with intensifying screens for 2–4 days at −70° C. To control for differences in the amount of RNA loaded, as well as the integrity of RNA, blots were stripped and probed with [$^{32}$P]-labeled cDNA for G3PDH. As shown in FIG. 1, the cDNA probe detected a species of rat mRNA that was 2.1 kb, expressed abundantly in 6-day old cerebellum and brain, but at low levels (3-fold less than at 6-days) in adult cerebellum.

Figure 2A:
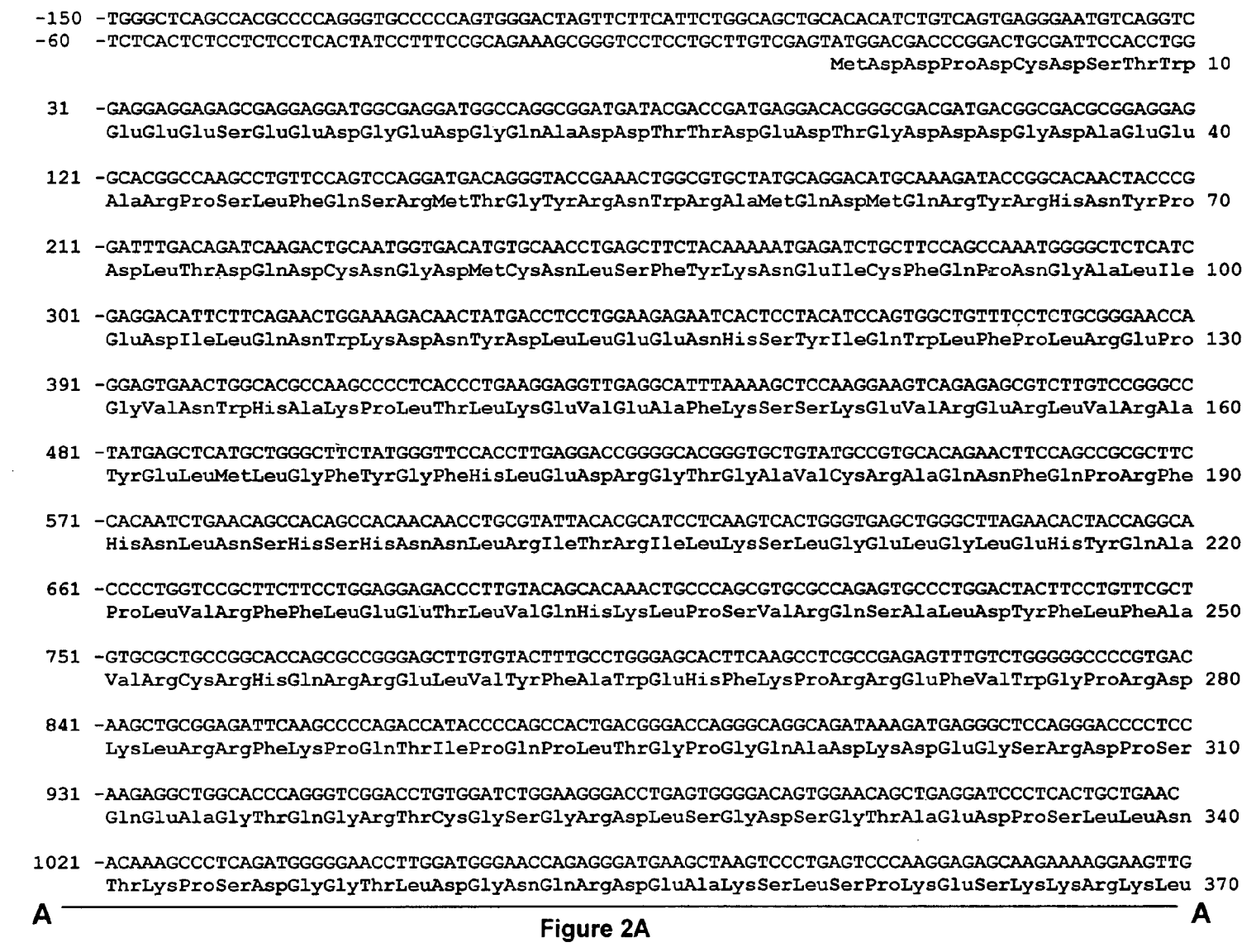

Since the #14 clone was not full length, labeled #14 cDNA was used as a hybridization probe to screen the λgt11 fetal rat brain library for full-length clones. Thirteen positive clones were identified and purified from the library by colony hybridization. Digestion of the purified clones with EcoR1 released a full size insert of 2.1 kb from clone #12. The #14 and the #12 cDNAs were sequenced in both directions. FIGS. 2A–2B show the nucleotide sequence (SEQ ID NO: 1), and the deduced amino acid sequence (SEQ ID NO: 2), of the full length cDNA, #12; 5' and 3' untranslated regions have been included. The open reading frame was found to encode a protein of 580 amino acids, with 8 imperfect repeat units of 9 amino acids at positions 467 to 538. The molecular weight as calculated from the sequence is 58 kD. Search of the sequences in GenBank revealed no homology to this cDNA.

EXAMPLE 2

Characterizing the OGF Receptor

Binding Assays

Inserts from clone #14 encoding the C-terminal 197 amino acids of rat OGFr, and from clone #12 encoding all 580 amino acids of rat OGFr, were ligated into the pGEX-3X expression vector (Promega, Madison, Wis.) to generate glutathione-S-transferase (GST) fusion proteins, referred to herein as 14-GST and 12-GST, respectively. When expressed in XL1-Blue strain bacteria (Stratagene, La Jolla, Calif.), and induced with isopropyl b-o-thiogalactopyranoside for 3 hr, these plasmids produced GST-OGF-binding fusion proteins which were then purified from crude bacterial extracts using glutathione affinity chromatography and 1-dimensional PAGE gel electrophoresis.

These fusion proteins were used in binding assays with [$^3$H]-[Met$^5$]-enkephalin (Zagon et al., Brain Res. 551: 28–35, 1991; Zagon et al., Brain Res. 605: 50–56, 1993). Fusion proteins (80–120 ng/tube) were incubated for 30 min with shaking at 22° C. Non-specific binding was measured in the presence of unlabeled [Met$^5$]-enkephalin. In some assays, NTX ($10^{-3}$ M) was added to the reaction mixture to monitor opioid antagonist blockade of binding. Binding was terminated by filtering homogenates through Whatman GF/B filters. Saturation isotherms were plotted using Graph-Pad Prism software (GraphPad Software Inc., San Diego, Calif.).

Figure 3:
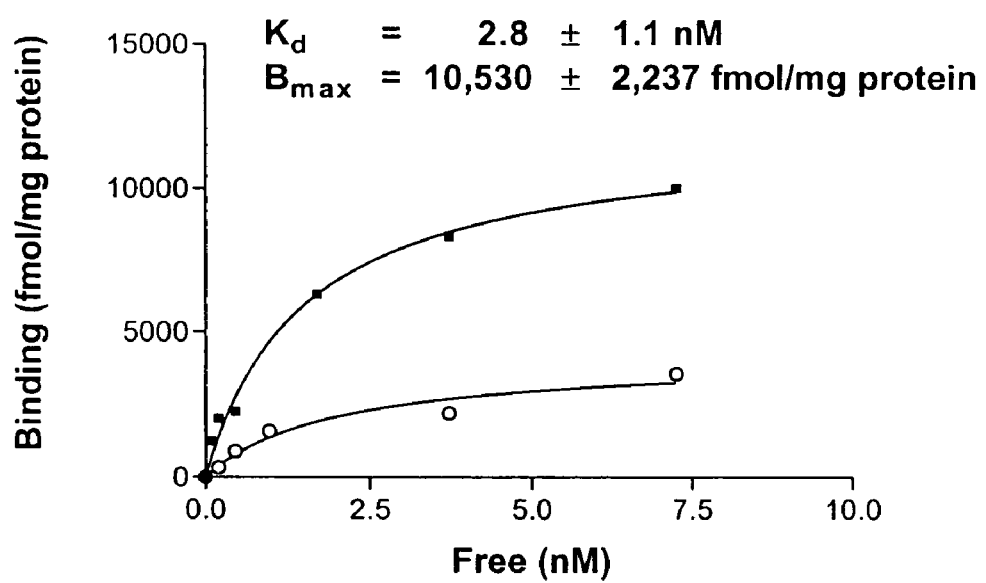
FIG. 3 depicts representative saturation isotherm of specific binding of [$^3$H]-[Met$^5$]-enkephalin (square) to purified fusion protein translated in vitro from the rat OGFr cDNA clone #12. Mean±SE binding affinity ($K_d$) for 6 assays was 2.8±1.1 nM and binding capacity ($B_{max}$) was 10,530±2,237 fmol/mg protein. Binding was significantly reduced with the addition of 1 mM concentrations of the opioid antagonist naltrexone (circle).
Figures 4A, 4B, 4C, 4D:
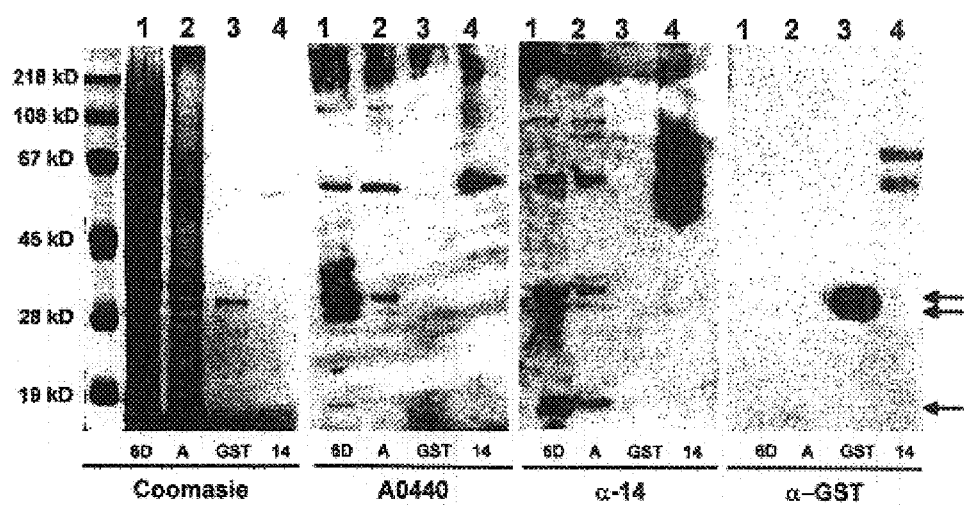
FIGS. 4A–4D depict the detection of six-day old (lane 1) and adult (lane 2) rat cerebellar nuclear proteins, native GST protein (lane 3), and recombinant GST-14e protein (lane 4) separated by SDS-PAGE and electrotransferred to nitrocellulose. A: Coomassie blue stained gel of the electrophoresed proteins. B–D: Western blots stained with polyclonal antibody generated against a 17-kD OGF binding protein (B), antibody made to fusion protein 14e (C), or antibody to GST (D). The staining patterns in panels B and C are similar. The blot in panel D demonstrates the specificity of the fusion protein antibody. The control antibody to GST detected GST and GST-fusion proteins, but not native nuclear homogenate. Arrows indicate the 62, 32, 30 and 17/16 kD OGF binding proteins.

Specific competition of 12-GST fusion protein was determined in the presence of a range ($10^{-10}$ to $10^{-3}$ M) of ligands including [D-Ala$^2$ MePhe$^4$, Glyol$^5$]-enkephalin (DAMGO), [D-Pen$^{2,5}$]-enkephalin (DPDPE), dynorphin A1–8, U69, 583, and morphine sulfate (FIG. 3). Specific and saturable binding was observed, with a mean binding affinity ($K_d$) of 2.8±1.1 nM and binding capacity ($B_{max}$) of 10,530±2,237 fmol/mg protein. Addition of naltrexone to the preparations significantly reduced specific and saturable binding, with reductions in $B_{max}$ of 83% noted (FIG. 3). Representative Scatchard plot of specific binding of radiolabeled [Met$^5$]-enkephalin revealed a one-site model of binding.

Using a variety of ligands that recognized classical opioid receptors, no competitive binding (>$10^3$ M) for radiolabeled [Met$^5$]-enkephalin by DAMGO or morphine sulfate (μ receptor), DPDPE (δ receptor), dynorphin A1–8 and U69, 583 (κ receptor) was observed.

Western Blotting

Antibodies against the recombinant fusion proteins were generated by inoculating New Zealand white rabbits with 14-GST or with 12-GST fusion proteins suspended in Freund's adjuvant. The GST was not cleaved from the proteins prior to inoculating the rabbits, allowing the GST to function as a carrier protein. Rabbits were injected every 4 weeks for 2 months, tested for their titer, and exsanguinated 4 days after the final injection.

Nuclear preparations of 6-day and adult rat cerebellum, as well as GST and 14-GST fusion proteins, were isolated by 12.5% SDS PAGE, and electrotransferred to nitrocellulose. Western blotting performed with primary antibodies to either the 14-GST fusion protein (Zagon et al., Brain Res. 630: 295–302, 1993), native OGF binding protein, or GST; [$^{125}$I]-protein A was used for antibody detection.

Antibodies to the recombinant fusion protein derived from clone #14 (14-GST) were titered and 1:1000 dilutions detected 10 ng of fusion protein. When reacted with nuclear preparations of 6-day old cerebellum on a 1-dimensional Western blot, anti-14-GST recognized 5 polypeptides: 62, 32, 30, 17, and 16 kD, as well as the recombinant protein (FIGS. 4A–4D). Western blots stained with antibodies generated against the native 32 kD binding protein detected the 62, 32, 30, 17, and 16 kD polypeptides, in addition to the recombinant protein (FIGS. 4A–4D). The antibody to the recombinant fusion protein or the native 32 kD polypeptide stained homogenates of the adult rat cerebellum, but was of a notably lesser density than in the 6-day specimen (FIGS. 4A–4D).

Immunocytochemistry

Immunocytochemistry was performed using methodology described previously (Zagon et al., *Brain Res.* 803: 61–68, 1998). In brief, rat brains from 6-day old and adult animals were frozen and sectioned. Adjacent sections were stained with antibodies to 14-GST fusion protein or with polyclonal antibodies to the OGF binding protein. Controls included staining sections with primary antibodies preabsorbed with either 14-GST fusion protein or with OGF binding protein, as well as secondary antibodies only.

Figure 5A:
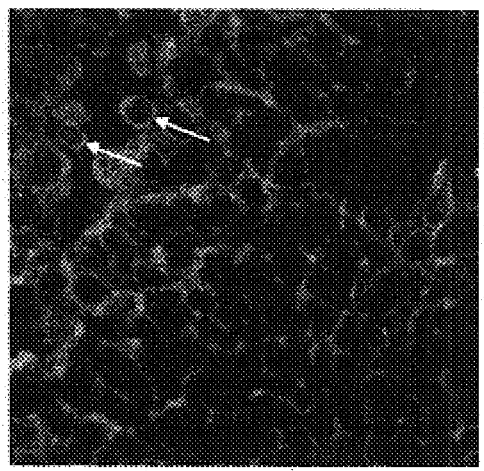
FIGS. 5A–5C depict distribution of OGFr in external germinal cells in adjacent midsagittal sections of 6-day old rat cerebellum (A, B) as detected by an antibody to the fusion protein 14e (A) or an antibody to the native 17-kD OGF binding protein (B). Internal granule cells in adult rat cerebellar sections stained with antibody to the fusion protein (14e) (C) revealed no immunoreactivity. Arrows=immunoreactivity. Bar=50 mm.
Figure 5B:
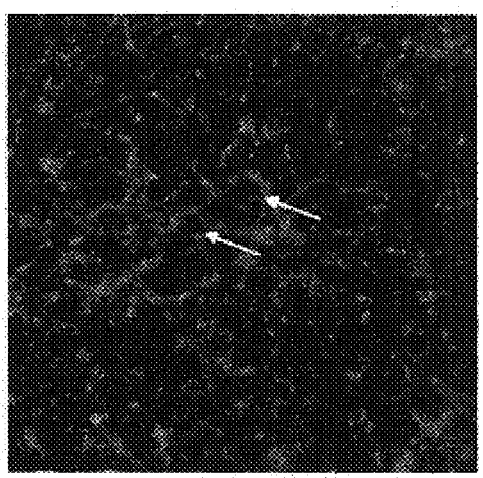
Figure 5C:
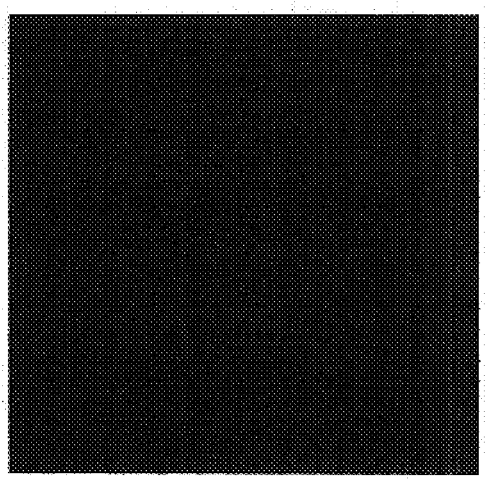

The staining pattern in immunocytochemical preparations employing antibodies to the recombinant fusion protein was similar to that observed when using antibodies to the authentic binding protein (FIGS. 5A–5C). Both antibodies revealed immunoreactivity in the 6-day old rat cerebellum, with cells of the external germinal layer exhibiting prominent staining of the cytoplasm and low reactivity of the nucleoplasm. The internal granule cells of adult rat cerebellar tissues demonstrated little specific immunoreactivity with either antibody.

EXAMPLE 3

Regulation of Cell Growth Using Rat OGFr Antisense DNA

In order to study the function of the isolated cDNA with respect to growth, a 23-mer antisense S-ODN (nuclease-resistant phosphorothioate; Oligo, Etc., Bethel, Me.) targeted against a sequence containing the translation initiation site of the OGF binding protein was designed: 5'-GACT-CAGGGACTTAGCTTCATCC-3' (antisense, SEQ ID NO: 15). A 23-mer with a scrambled sequence was also designed: 5'-ATAGATACTACGCCGGCTGTCCT-3' (scrambled, SEQ ID NO: 16).

The IEC-6 rat small intestine epithelial cell line (American Type Tissue Culture Collection, Manassas, Va.) were grown in Dulbecco's medium supplemented with 10% fetal calf serum. For experiments, $5 \times 10^3$ cells/well in a 24-well plate were seeded and, 24 hr later, $10^{-6}$ M concentrations of the antisense or the scrambled S-ODN were added. Some wells were exposed to $10^{-6}$ NTX or an equivalent volume of sterile water. Media, S-ODNs, or drugs were changed daily. After 72 hr in culture, cells were trypsinized, stained with trypan blue, and counted with a hemacytometer; 3 wells/ treatment group were assessed. The data were evaluated with ANOVA, and subsequent comparisons were made with the Newman-Keuls tests.

Figure 6:
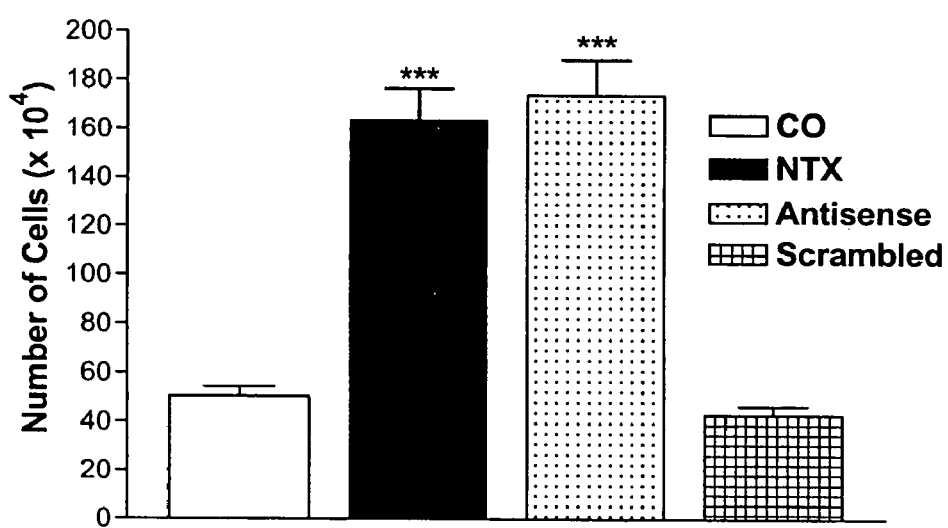
FIG. 6 depicts histogram of cell number in cultures of IEC-6 rat intestinal epithelial cells treated for 48 hr with either sterile water (CO), 10$^{-6}$ M NTX, 10$^{-6}$ M 23-mer S-ODN (antisense), or scrambled oligoprobe (scrambled). Cells (5×10$^3$) were plated, and compounds and fresh media were added 24 hr and 48 hr later. After 72 hr in culture, cells were trypsinized, stained with trypan blue, and counted with a hemacytometer. Data of different sets are significantly different (p<0.001).

As shown in FIG. 6, the antisense S-ODN elevated cell number by 294% from control cultures within 48 hr of exposure. The cell cultures treated with the scrambled probe were similar in growth to control levels. Cultures treated with NTX, an antagonist to the opioid binding protein, also demonstrated increased cell growth from control values; the NTX group had 223% more cells than control cultures. The cells treated with scrambled message were comparable to controls in cell number.

EXAMPLE 4

Isolation of cDNA Encoding a Human OGF Binding Protein

A fragment of the human OGFr cDNA was obtained by reverse transcriptase—polymerase chain reaction (RT-PCR) using mRNA from a pool of 24 male/female, 20–25-week old human fetal brains obtained from spontaneous abortions (Clontech, Palo Alto, Calif.). Primers were generated from the rat cDNA sequence (clone #12, Example 1). A RT-PCR product of 400 nucleotides (as predicted) was amplified and designated "H5". Homology with rat OGFr was confirmed by Southern blot analysis using [$^{32}$P]-dCTP labeled rat clone #12. H5 was cloned using the TOPO TA cloning kit (Invitrogen, Carlsbad, Calif.) and sequenced. RNA from a variety of human tissues was probed with [$^{32}$P]-dCTP labeled H5, and revealed that the greatest amount of target mRNA was associated with human placenta.

Figure 7A:
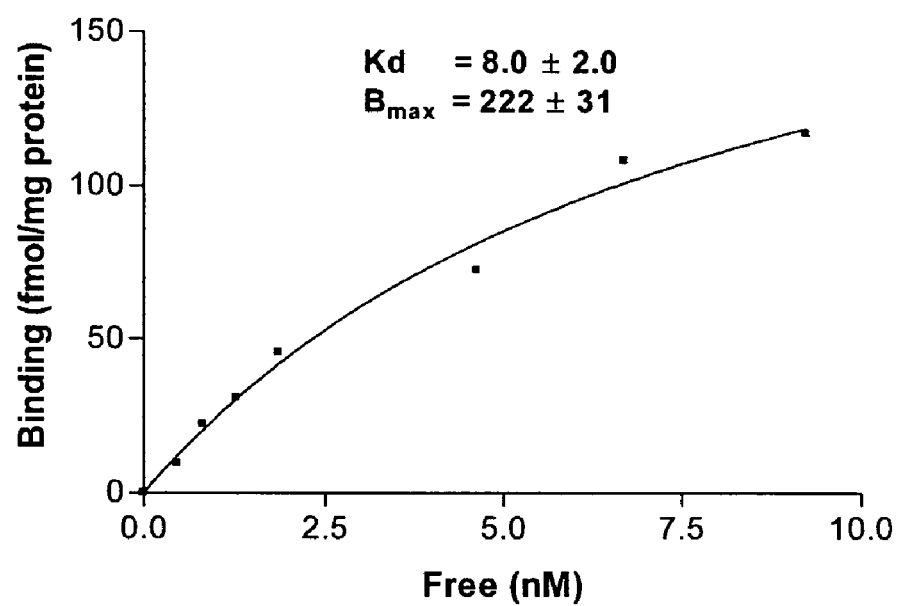
FIGS. 7A–7B depict representative saturation isotherm and Scatchard plot (inset) of specific binding of [$^3$H]-[Met$^5$]-enkephalin to a nuclear-enriched fraction of human placenta. A one-site model of binding was noted.
Figure 7B:
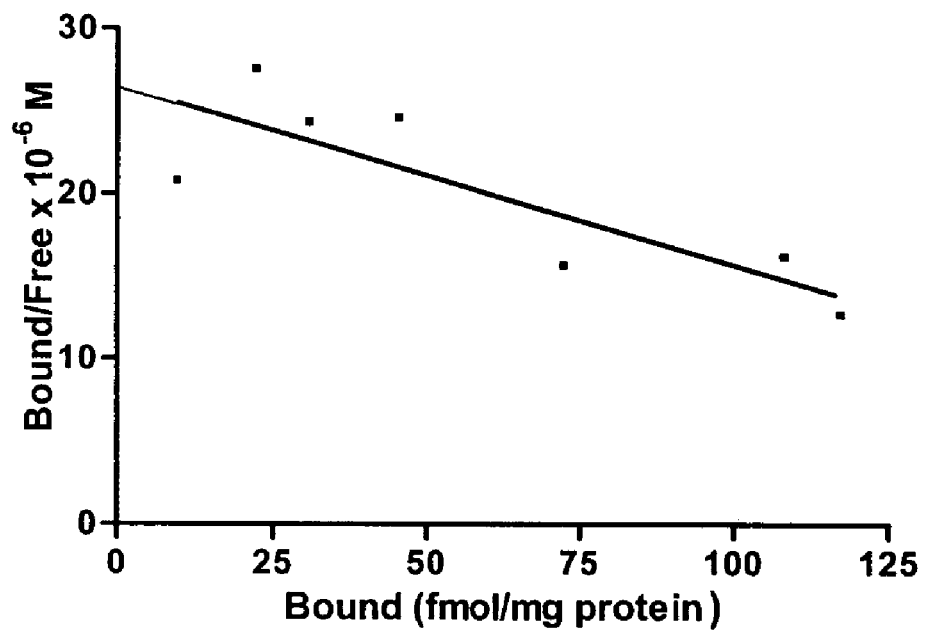

Binding assays were performed on human placenta using radiolabled [Met$^5$]-enkephalin to characterize this tissue. Binding studies with human placenta and radiolabeled [Met$^5$]-enkephalin revealed specific and saturable binding, with a mean binding affinity ($K_d$) of 12.3±3.9 nM and a binding capacity ($B_{max}$) of 247±95 fmol/mg protein (FIGS. 7A–7B). A one-site model of binding was noted.

Using human placental mRNA (Clontech), the complete sequence of human OGFr was assembled with a combination of 3'- and 5'-RACE techniques performed with a Marathon cDNA Amplification Kit (Clontech). RACE products were cloned utilizing a TOPO TA cloning kit (Invitrogen) and sequenced by an automated sequencer (ABI Prism Model 377 Version 2.1.1) located in the MacroMolecular Facility of The Pennsylvania State University College of Medicine. Sequence data were analyzed with the Sequence Analysis Software Package of the Genetics Computer Group (University of Wisconsin Biotechnology Center).

5' RACE consistently yielded a single species of cDNA, while the 3' RACE revealed extensive alternative splicing. When assembled, the longest predicted cDNA (designated clone 8 for the particular 3' clone found with a given structure) was 2.4 kb. FIG. 8A shows the nucleotide (SEQ ID NO: 5) and the deduced amino acid sequence (SEQ ID NO: 6) of this cDNA; 5' and 3' untranslated regions have been included. The open reading frame was found to encode a protein of 697 amino acids, and 8 imperfect repeats of 20 amino acids were a prominent feature. The predicted initiation site was flanked by a strong Kozak consensus sequence. A number of alternate spliced forms were detected by 3' RACE, and these are depicted in FIGS. 8B–D. Two of the alternate spliced forms (clones #1 and 127) were missing the imperfect repeats (FIG. 8C). Clones #4, 7, and 8 differed only in the number of imperfect repeats (FIG. 8D).

Sequence similarity was compared to the entries recorded in the GenBank database using FASTA and BLAST databases.

The chromosomal location of the human receptor for OGF was determined by FISH as 20q13.3 (FIG. 8E).

EXAMPLE 5

Expression Pattern of Human OGFr

Northern blot analysis of human fetal and adult tissues, as well as cancer tissues and cell lines, was performed with a radiolabeled OGFr cDNA cocktail according to the procedure described by McLaughlin and Allar (*Mol. Brain Res.* 60: 160–167, 1998).

Briefly, commercially prepared blots of poly A$^+$ RNA from human tissues and cells were obtained from Clontech (Palo Alto, Calif.). RNA samples of fetal tissue (Human Fetal II Multiple Tissue Northern (MTN™) Blot, Lot. #080009) were pooled from tissues ranging from 7 to 32 individuals that were 16 to 32 weeks in age, and representative of both genders. The cause of death was spontaneous abortion. The blot of human tissues (Human Multiple Tissue Northern (MTN™) Blot, Lot #8070732) contained pooled samples from 2 to 18 individuals that were 10 to 69 years in age and, except for the heart (males) and placenta (females), was representative of both genders. In the case of the liver, the tissue was obtained from a 35-year-old male. With the exception of the placenta, the causes of death were reported as sudden death (brain, lung, liver, and skeletal muscle) or trauma (heart, kidney, and pancreas). A Human Cancer Cell Line Multiple Tissue Northern (MTN™) Blot (Lot #9050001) was purchased from Clontech and contained: promyelocytic leukemia, HL-60, HeLa cell S3, chronic myelogenous leukemia K-562, lymphoblastic leukemia MOLT-4, Burkitt's lymphoma Raji, colorectal adenocarcinoma SW480, lung carcinoma A549, and melanoma G361. Cancer cell lines were purchased from the American Type Tissue Collection (Manassas, Va.) and included: human pancreatic cancer cell lines BxPC3, PANC-1, and MIA PaCa-2, squamous cell carcinoma of the head and neck CAL-27, and neuroblastoma SK-N-SH. Human pancreatic total RNA was purchased from InVitrogen (Lot #7110156). Surgical specimens of human tissues included: squamous cell carcinoma of the tongue (65-yr-old male, Stage III), renal cell carcinoma and normal kidney (73-yr-old male, radical nephrectomy).

Total RNA was prepared by immersing preparations in ice-cold 4 M guanidinium isothiocyanate/0.83% β-mercaptoethanol/0.3 M sodium acetate and homogenizing with a polytron (setting 6, 2×10 sec). Homogenized tissues were layered over a cushion of 5.7 M cesium chloride/0.3 M sodium acetate and centrifuged at 105,000×g with an SW55Ti rotor for 18 hr at 25° C. Total RNA was precipitated with ethanol, and quantitated by UV spectrometry. Inasmuch as possible, equal amounts of total RNA were subjected to electrophoresis on 1.0% agarose-2.5% formaldehyde gels, transferred by capillary blotting to nylon membranes, and baked in vacuo at 80° C. for 1 hr. Filters were prehybridized for 4–8 hr at 42° C. in a solution containing 50% deionized formamide, 5× Denhardt's buffer (50× Denhardt's=5 g Ficoll, 5 g polyvinylpyrrolidone, and 5 g bovine serum albumin in 500 ml sterile water), 50 mM sodium phosphate, pH 6.5, 5× SSC (20× SSC=3 M sodium chloride and 0.3 M sodium citrate), 500 mg/ml salmon sperm DNA (Sigma) and 1% SDS.

Membranes were hybridized at 42° C. for 22 hr in fresh prehybridization buffer containing 10$^6$ cpm/ml of random primed human cDNAs. Filters were subjected to final washes at 60° C. with 0.1× SSC containing 0.1% SDS for 30 min, and wrapped in plastic while wet, and exposed to autoradiography film with intensifying screens for 2–4 days at –70° C. To control for differences in the amount of RNA loaded, as well as the integrity of RNA, blots were stripped and probed with [$^{32}$P]-labeled cDNA for β-actin (Clontech).

As shown in FIGS. 9A–9D, in the human fetal tissues, transcript sizes of 1.7 and 2.4 kb were observed, whereas in the adult tissues and cancer cell lines and tissues only a 2.4 kb mRNA was detected. Receptor for OGF was of low abundance only in adult lung.

EXAMPLE 6

Regulation of Cell Growth Using Human OGFr Antisense DNA

To study the function of the isolated cDNA with respect to regulation of cell growth, a 23-mer antisense S-ODN (nuclease-resistant phosphorothioate; Oligo, Etc., Bethel, Me.) targeted against a sequence containing the translation initiation site of the OGF binding protein was designed: 5'-GGTCGTCCATGCTCGGCTAGAAT-3' (antisense, SEQ ID NO: 17). A scrambled (control) S-ODN was also designed: 5'-GTGCAGTGCAATGCTCTCCGTGA-3' (SEQ ID NO: 18).

The SK-N-AS human neuroblastoma cell line (American Type Tissue Culture Collection, Manassas, Va.) was grown in Dulbecco's medium supplemented with 10% fetal calf serum. For experimentation, 6×10$^3$ cells/well in a 24-well plate were seeded and, 24 hr later, 10$^{-6}$ M concentrations of the antisense or the scrambled S-ODN was added. Some wells were exposed to 10$^{-6}$ M NTX or an equivalent volume of sterile water. Media, S-ODNs, or drugs were changed daily. After 72 hr in culture, cells were trypsinized, stained with trypan blue, and counted with a hemacytometer. Data from the antisense experiments were evaluated with ANOVA, and subsequent comparisons made with the Newman-Keuls tests.

As shown in FIG. 10, the antisense S-ODN elevated cell number by 60% from control cultures within 48 hr of exposure. The cell cultures treated with the scrambled probe were similar in growth to control levels. Cultures treated with NTX, an antagonist to the opioid binding protein, also had increased cell growth from control values.

EXAMPLE 7

Characterization of OGFr in Human Pancreatic Adenocarcinoma

Materials and Methods

Cell culture. PANC-1, Mia PaCa-2, BxPC-3, and Capan-1 cell lines were obtained from the American Type Culture Collection (Manassas, Va.). Specific characteristics of each human pancreatic tumor cell line have been reported previously (Zagon et al., *Int. J. Oncol.* 14: 577–584, 1999). PANC-1 and MIA PaCa-2 cells were maintained in Dulbecco's modified media, while Capan-1 and BxPC-3 cells were grown in RPMI media; all media contained 10% fetal calf serum, 2 mM L-glutamine, 1.2% bicarbonate and antibiotics (5,000 Units/ml penicillin, 5 mg/ml streptomycin, 10 mg/ml neomycin). Cells were grown in a humidified atmosphere of 5% $CO_2$/95% air at 37° C. Panc-1 cells between passages 62–74 were used for the characterization studies.

Preparation of protein fractions. Cell cultures were harvested by scraping of the flasks, and cells were pelleted by centrifugation. The washed pellet was homogenized (Polytron, setting 5, 2×10 sec) in a 1:20 (wt/vol) solution of cold 50 mM Tris-HCl with 0.1 mg/ml bacitracin, 1 mg/ml leupeptin, 6 nM thiorphan, 1 mM EGTA, and 3.5 mM PMSF (pH 7.4) at 4° C.; this buffer is termed Tris/all. Homogenates were layered over a 1.4 M sucrose cushion, and centrifuged (2,200 g) for 20 min; this step was conducted twice in order to obtain a nuclear pellet (P1).

For subcellular fractionation studies, the supernatant of P1 was centrifuged at 39,000× g for 30 min to obtain a plasma membrane pellet (P2). The P2 supernatant was centrifuged overnight (100,000× g), resulting in a microsomal pellet (P3) and soluble supernatant (S3). All fractions were inspected for purity by phase-contrast microscopy.

Receptor binding assays. Homogenates of nuclear protein were diluted with Tris/all to the appropriate protein concentration and incubated at room temperature (22° C.) for 20 min to remove endogenous peptides. Aliquots of protein were resuspended to 0.95 ml and incubated with agitation with radioactive ligand. Saturation assays were conducted with various concentrations of ligand, usually ranging from 0.1 to 15 nM. The final volume of the incubation mixture was 1 ml. Isotope incubation was terminated by rapid filtration through Whatman GF-B filters under vacuum pressure with a Brandel Cell Harvester. Filters were rinsed with ice-cold Tris/all buffer, dried at 60° C. for 1 hr and counted by liquid scintillation spectrometry (Beckman LS-2800). Nonspecific binding was determined in the presence of 100 nM of [Met$^5$]-enkephalin. Duplicate tubes of homogenates were assayed for each concentration utilized. Protein concentrations were determined by the BioRad method with g-globulin as the standard.

For competition studies, nuclear homogenates were incubated with 1 nM radiolabeled [Met$^5$]-enkephalin and a range of concentrations ($10^{-4}$ to $10^{-10}$ M) of each of the nonlabeled compounds. Each concentration was run in triplicate and every compound was tested twice.

Analysis and statistics. Receptor binding data were analyzed with either the Lundon I (Saturation Isotherm Binding Analysis) computer program (Lundon Software, Cleveland, Ohio) or GraphPad Prism software. Both programs utilize nonlinear least-squares regression. Binding isotherms and Scatchard plots were computed directly by the programs. Competition data were analyzed by the Lundon II competition data-analysis program, and the inhibition constant was calculated from the half-maximal displacement (concentration inhibiting 50% of maximal response) values using the method of Cheung and Prusoff (*Biochem. Pharmacol.* 22: 3099–3108, 1973). Comparisons of $B_{max}$ and $K_d$ values were made using analysis of variance and posthoc Newman-Keuls tests.

Characterization of [$^3$H]-[Met$^5$]-enkephalin Binding

The optimal conditions for binding of [$^3$H-[Met$^5$]-enkephalin (OGF) to PANC-1 nuclear (P1) homogenates were determined. Specific binding of radiolabeled ligand to PANC-1 nuclear homogenates was dependent on protein concentration and was linear between 200 and 550 mg/ml (FIG. 12). Binding of $^3$H-[Met$^5$]-enkephalin to P1 homogenates of PANC-1 cells was also dependent on time and temperature of incubation (FIG. 13). Maximal specific binding occurred at 22° C., reaching an equilibrium between 60–75 min. Binding at 0° C. and 37° C. was 12% and 21%, respectively, of the optimal binding at 22° C. The binding of radiolabeled [Met$^5$]-enkephalin was also dependent on pH of the buffer solution, with an optimal pH of 7.4 being recorded (FIG. 14).

The effects of monovalent and divalent cations on [$^3$H]-[Met$^5$]-enkephalin binding to PANC-1 nuclear homogenates are presented in FIG. 15. Addition of NaCl, CaCl$_2$, and MgCl$_2$ at concentrations of 50, 100, or 200 mM reduced specific radioactive binding by as much as 85%. The binding of [$^3$H]-[Met$^5$]-enkephalin was not markedly altered by addition of 50, 100, or 200 μM GppNHp to the binding assays.

By use of the optimal conditions for protein concentration, time, temperature, and pH described above, in a buffer containing a cocktail of protease inhibitors, [$^3$H]-[Met$^5$]-enkephalin binding to PANC-1 nuclear homogenates (P1 fraction) was found to be specific and saturable (FIGS. 16A–16B). Computer analysis of binding showed that the data best fit a one-site binding model with an average equilibrium dissociation constant ($K_d$) of 1.2±0.3 nM and a mean maximal binding capacity ($B_{max}$) of 36.4±4.1 fmol/mg protein. Nonspecific binding was calculated to be ~52% of the total binding.

Competition Assays

Competition experiments using 1 or 2 nM [$^3$H] [Met$^5$]-enkephalin and a range of natural and synthetic opioid peptides were performed to examine the specificity and relationship of radiolabeled [Met$^5$]-enkephalin to its binding site (Table I). [Met$^5$]-enkephalin exhibited the greatest potency of any of the compounds tested, having 100-fold greater ability to displace [$^3$H] [Met$^5$]enkephalin than the next ranking compound; the competition value (IC$_{50}$) for [Met$^5$]-enkephalin was 5.5 nM. Ligands related to the μ—(i.e., DAMGO), δ—(i.e., DPDPE, ICI-174,468), κ—receptors (i.e., dynorphin A, U69,598, ethylketocyclazocine), and well as morphine and leucine enkephalin exhibited little or no competition.

TABLE I

Potency of prototypic opioid ligands to compete for binding of [$^3$H]-[Met$^5$]-enkephalin in nuclear homogenates of human pancreatic tumor cells (PANC-1).

| | Compound | IC$_{50}$/K$_d$ |
|---|---|---|
| μ Receptor | DAMGO | >10$^{-4}$ |
| δ Receptor | DPDPE | >10$^{-4}$ |
| | ICI-174,568 | >10$^{-4}$ |
| κ Receptor | Dynorphin A1-8 | >10$^{-4}$ |
| | U69,598 | >10$^{-5}$ |
| | EKC | >10$^{-3}$ |
| Other ligands | Morphine | >10$^{-3}$ |
| | Leucine enkephalin | >10$^{-4}$ |
| | β-endorphin | >10$^{-4}$ |

Data represent values from at least 2 independent assays.
Equilibrium dissociation constants for [Met$^5$]-enkephalin was 1.2 ± 0.3 nM.
IC$_{50}$ is the concentration that inhibits 50% of maximal response; $_{KD}$ is the inhibition constant.
DAMGO = [D-Ala$^2$, N-Me-Phe$^4$, Gly$^5$-ol]-enkephalin, DPDPE = [D-Pen$^2$, Pen$^5$]-enkephalin, EKC = ethylketocyclazocine.

Data represent values from at least 2 independent assays. Equilibrium dissociation constant for [Met$^5$]-enkephalin was 1.2±0.3 nM. IC$_{50}$ is the concentration that inhibits 50% of maximal response; m is the inhibition constant. DAMGO=[D-Ala$^2$, N-Me-Phe$^4$, Gly$^4$-ol]-enkephalin, DPDPE=[D-Pen$^2$, Pen$^5$]-enkephalin, EKC=ethylketocyclazocine.

Subcellular Fractionation Studies

Sucrose gradient centrifugation was performed to separate the nuclear (P1), membrane (P2), microsomal (P3), and soluble (S3) fractions (Table II). In these experiments, specific and saturable binding of [$^3$H]-(Met$^5$)-enkephalin was detected in the P1 fraction, and computer analysis revealed a one-site model of binding with a $K_d$ of 2.3±0.5 nM and $B_{max}$ of 21.8±4.8 fmol/mg protein. No specific and saturable binding was detected in fractions enriched in the P2, P3, or S3 fractions.

TABLE II

Subcellular fractionation studies utilizing [$^3$H]-[Met$^5$]-enkephalin and PANC-1 human pancreatic cells.

| Fraction | Cellular Composition | $K_d$, nM | $B_{max}$ (fmol/mg protein) |
|---|---|---|---|
| P1 | Nuclear | 2.3 ± 0.5 | 21.8 ± 4.8 |
| P2 | Membranes | NB | NB |
| P3 | Microsomal | NB | NB |
| S3 | Soluble | NB | NB |

Values represent means ± SE for 3 independent assays.
$K_d$, dissociation constant;
$B_{max}$, binding capacity.
NB = no specific or saturable binding.

Stage of Growth on PANC-1 Cells

PANC-1 cells grown for 3 to 4 days (log phase), 6–7 (confluent), or 9 days (post-confluent) were assayed for binding to radiolabeled [Met$^5$]-enkephalin (Table III). The length of time in culture had no effect on the affinity of [$^3$H]-[Met$^5$]-enkephalin. However, in contrast to post-confluent cells, the binding capacity of radiolabeled [Met$^5$]-enkephalin was reduced by 42% and 78% from the log-phase and confluent cultures, respectively.

TABLE III

Binding of [$^3$H] - [Met$^5$] - enkephalin and PANC-1 human pancreatic cells at different stages of growth.

| | Days in culture | $K_d$, nM | $B_{max}$ (fmol/mg protein) |
|---|---|---|---|
| Log phase | 3 | 4.2 ± 2.1 | 20.7 ± 1.2 |
| Confluent | 5 | 5.3 ± 0.0 | 7.8 ± 0.0** |
| Post-confluent | 7–8 | 13.1 ± 1.1 | 35.6 ± 0.3** |

Values represent means ± SE for 3 independent assays.
$K_d$, dissociation constant; $B_{max}$, binding capacity.
**Significantly different from log phase at p < 0.01.

Values represent means±SE for 3 independent assays. $K_d$, dissociation constant; $B_{max}$, binding capacity. **Significantly different from log phase at p<0.01.

Ubiquity of OGFr in Pancreatic Cancer Cell Lines and Xenografts

To examine for the presence of OGFr in a variety of pancreatic adenocarcinoma, saturation binding isotherms were performed on nuclear homogenates obtained from log phase BxPc-3, MIA PaCa-2, Capan-1, and Capan-2 cells (Table IV). The $K_d$ ranged from 1.2 to 10.8 nM, and the $B_{max}$ ranged from 11.9 to 25.5 fmol/mg protein.

Xenografts of human pancreatic cancer were performed according to earlier procedures (Zagon et al., Cancer letters 112: 167–175, 1997). In brief, 200,000 log-phase Capan-1 were injected subcutaneously into 4-week-old athymic nude mice (Charles River Laboratories, Wilmington, Mass.). Tumor tissue was harvested 40 days after cell inoculation. Xenografts of Capan-1 growing in nude mice revealed a $K_d$ of 2.9±1.5 nM and a $B_{max}$ of 4.2±1.1 fmol/mg protein.

TABLE IV

Specific binding for [$^3$H]-[Met$^5$]-enkephalin to nuclear fractions of a variety of human pancreatic cancer cell lines.

| Cell Line | State of Differentiation | $K_d$, nM | $B_{max}$, fmol/mg |
|---|---|---|---|
| MIA PaCA-2 | Moderately to well | 10.8 ± 5.5 | 11.9 ± 1.5 |
| Capan-1 | Metastatic to liver | 6.5 ± 4.1 | 22.7 ± 9.5 |
| BxPC-3 | Moderately to well | 1.2 ± 0.3 | 25.5 ± 9.7 |
| PANC-1 | Poor | 5.1 ± 1.4 | 28.9 ± 6.2 |

Values represent means ± SE for at least 3 independent assays.
$K_d$, dissociation constant;
$B_{max}$, binding capacity.

OGFr in Neoplastic and Normal Pancreatic Tissues

Tumor specimens were obtained at the time of pancreatic resection from four females ranging in age from 52- to 66-yrs, and a 67-yr-old male. Normal tissues (as determined from histological assessment) were obtained from two females (61- and 66-yr-old) and a male (55-yr-old). In the case of the normal samples from the two females, the specimens were adjacent to the tumor tissue. All human tissue specimens were collected with the approval of the Institutional Review Board, Human Subjects Protection Office, The Pennsylvania State University College of Medicine. Samples were collected and frozen in liquid nitrogen within 1 hr of surgery. Receptor binding assays were performed as stated above.

Human pancreatic cancer obtained at resection showed a mean $K_d$ of 2.1±1.0 nM and a $B_{max}$ of 6.6±1.2 fmol/mg protein for the specimens harvested from 3 patients; in 3 specimens, non-specific and non-saturable binding were recorded. Of the 3 normal specimens of human pancreas, a mean $K_d$ of 9.6±2.9 and $B_{max}$ of 46.7±27.8 fmol/mg protein was detected.

EXAMPLE 8

Decreased OGFr Number in Head and Neck Squamous Cell Carcinoma Compared to Normal Mucosa To compare the ζ opioid receptor in SCCHN versus normal mucosa, pharmacological binding assays utilizing enriched nuclear preparations of human tissue obtained from surgery and [$^3$H]-[Met$^5$]-enkephalin were conducted. Specific and saturable binding of a one-site receptor model was confirmed. Human tissue samples were representative of a variety of squamous cell carcinomas, including specimens from the oral cavity-larynx, and regional metastases. Normal mucosal specimens were obtained during uvu-lo-palatopharyngoplasty. Binding capacity ($B_{max}$) of the radioactive ligand, and index of receptor number, was 80.8±32.8 fmol/mg protein for normal epithelium in comparison to a 6-fold less $B_{max}$ of 13.6±1.9 fmol/mg protein for neoplastic specimens; these values differed significantly (p<0.01). No differences in binding were noted among the carcinogenic tissues assayed. Specific affinity ($k_\alpha$) values were comparable between normal and neoplastic tissues being 11.6±2.5 and 4.1±0.4 nM respectively. These data indicate that opioid growth factor receptor levels are reduced in human SCCHN when compared to normal mucosa. Nonetheless, the receptors are present and capable of binding ligand and with normal affinity suggesting that supplementation with exogenous OGF might be inhibitory to cancer cells.

We claim:

1. An isolated nucleic acid molecule comprising SEQ ID NO: 1 wherein said nucleic acid molecule encodes a polypeptide that binds to OGF.

2. An isolated nucleic acid molecule encoding a protein wherein said protein binds OGF and comprises the sequence as set forth in SEQ ID NO: 2.

3. An isolated nucleic acid molecule comprising SEQ ID NO: 9 wherein said nucleic acid molecule encodes a polypeptide that binds to OGF.

4. An isolated nucleic acid molecule encoding a protein wherein said protein binds OGF and comprises the sequence as set forth in SEQ ID NO: 10.

5. An expression vector comprising any one of the isolated nucleic acid molecules of claim 1, 2 or 3–4.

6. An isolated cell, transformed with the expression vector of claim 5.

7. A composition comprising the isolated nucleic acid molecule any of one of claim 1, 2 or 3–4 and a pharmaceutically acceptable carrier.

8. A composition comprising the expression vector of claim 5 and a pharmaceutically acceptable carrier.

9. A composition comprising the cell of claim 6 and a pharmaceutically acceptable carrier.

* * * * *

SEQUENCE LISTING

<160> NUMBER OF SEQ ID NOS: 18

<210> SEQ ID NO 1
<211> LENGTH: 2250
<212> TYPE: DNA
<213> ORGANISM: Rattus norvegicus

<400> SEQUENCE: 1

| | | | | | |
|---|---|---|---|---|---|
| tgggctcagc | cacgccccag | ggtgccccca | gtgggactag | ttcttcattc | tggcagctgc | 60 |
| acacatctgt | cagtgaggga | atgtcaggtc | tctcactctc | ctctcctcac | tatcctttcc | 120 |
| gcagaaagcg | ggtcctcctg | cttgtcgagt | atggacgacc | cggactgcga | ttccacctgg | 180 |
| gaggaggaga | gcgaggagga | tggcgaggat | ggccaggcgg | atgatacgac | cgatgaggac | 240 |
| acgggcgacg | atgacggcga | cgcggaggag | gcacggccaa | gcctgttcca | gtccaggatg | 300 |
| acagggtacc | gaaactggcg | tgctatgcag | gacatgcaaa | gataccggca | caactacccg | 360 |
| gatttgacag | atcaagactg | caatggtgac | atgtgcaacc | tgagcttcta | caaaaatgag | 420 |
| atctgcttcc | agccaaatgg | ggctctcatc | gaggacattc | ttcagaactg | gaaagacaac | 480 |
| tatgacctcc | tggaagagaa | tcactcctac | atccagtggc | tgtttcctct | gcgggaacca | 540 |
| ggagtgaact | ggcacgccaa | gcccctcacc | ctgaaggagg | ttgaggcatt | taaaagctcc | 600 |
| aaggaagtca | gagagcgtct | tgtccgggcc | tatgagctca | tgctgggctt | ctatgggttc | 660 |
| caccttgagg | accggggcac | gggtgctgta | tgccgtgcac | agaacttcca | gccgcgcttc | 720 |
| cacaatctga | acagccacag | ccacaacaac | ctgcgtatta | cacgcatcct | caagtcactg | 780 |
| ggtgagctgg | gcttagaaca | ctaccaggca | cccctggtcc | gcttcttcct | ggaggagacc | 840 |
| cttgtacagc | acaaactgcc | cagcgtgcgc | cagagtgccc | tggactactt | cctgttcgct | 900 |
| gtgcgctgcc | ggcaccagcg | ccgggagctt | gtgtactttg | cctgggagca | cttcaagcct | 960 |
| cgccgagagt | ttgtctgggg | gccccgtgac | aagctgcgga | gattcaagcc | ccagaccata | 1020 |
| ccccagccac | tgacgggacc | agggcaggca | gataaagatg | agggctccag | ggaccctcc | 1080 |
| caagaggctg | gcacccaggg | tcggacctgt | ggatctggaa | gggacctgag | tggggacagt | 1140 |
| ggaacagctg | aggatccctc | actgctgaac | acaaagccct | cagatggggg | aaccttggat | 1200 |
| gggaaccaga | gggatgaagc | taagtccctg | agtcccaagg | agagcaagaa | aaggaagttg | 1260 |
| gaggggaaca | gcaggagca | ggtcccaggg | gaggcagatc | cccagggtgt | ctctgaggta | 1320 |
| gagaaaattg | cccttaacct | tgaggagtgt | gcccttagcc | ctatcagcca | ggagcccagg | 1380 |
| gaggctgaac | cgccctgtcc | tgtggccagg | gtggctaatg | aggtaagaaa | gcggaggaag | 1440 |
| gtggaggaag | gggctgaggg | tgatggagta | gtcagtaaca | ctcaaatgca | ggccagtgcc | 1500 |
| ctgcctccta | ccccttcaga | gtgtcctgag | gcccaaaagg | atgggaatgg | gccagaggac | 1560 |
| tcaaacagcc | aggttgggc | agaggattcc | aaaagccagg | tggggccgga | ggatccaaac | 1620 |
| agccaggtgg | ggctggagga | cccaaacagc | caggtcgggc | cagaggaccc | aaacagccag | 1680 |
| gtcgggccag | aggacccaaa | cagccaggtc | gggccagagg | acccaaacag | ccaggtcggg | 1740 |
| ccagaggacc | caaacagcca | ggtggtgggg | ccagagcaag | ctgcctctaa | gagccctgtg | 1800 |
| gaggaccctg | actctgacac | tatgggaacc | tcagtggatg | agtcagagga | gttggcaagg | 1860 |
| attgaggcct | ctgctgaacc | cccaaagcct | tagaggtgca | tctcagtcct | actcagccca | 1920 |
| ctgcaggggg | tttctgagtc | cagagctctg | ccgtaggctc | ttcttggtgc | cccacagtgc | 1980 |
| tggcctctcc | ctagtggtca | ctgaggtggc | caccagaggg | actgaggccc | tgccctcagg | 2040 |

```
gaaggccaag gccttcagaa ccctccttac ctcactgtgt cctcctccac tgccctctga   2100
gccctgcgtt gtgatcagac cctaagggtc tagagggagg ggcctcttca ttagtctggt   2160
gccaagtgag gccttttctg aataaactct ttagactttg tcaaaaaaaa aaaaaaaaa    2220 aaaaaaaaaa aaaaaaaaaa aaaaaaaaaa                                    2250
```

<210> SEQ ID NO 2
<211> LENGTH: 580
<212> TYPE: PRT
<213> ORGANISM: Rattus norvegicus

<400> SEQUENCE: 2

```
Met Asp Asp Pro Asp Cys Asp Ser Thr Trp Glu Glu Ser Glu Glu
 1               5                  10                  15

Asp Gly Glu Asp Gly Gln Ala Asp Thr Thr Asp Glu Asp Thr Gly
                20                  25                  30

Asp Asp Asp Gly Asp Ala Glu Glu Ala Arg Pro Ser Leu Phe Gln Ser
             35                  40                  45

Arg Met Thr Gly Tyr Arg Asn Trp Arg Ala Met Gln Asp Met Gln Arg
 50                  55                  60

Tyr Arg His Asn Tyr Pro Asp Leu Thr Asp Gln Asp Cys Asn Gly Asp
 65                  70                  75                  80

Met Cys Asn Leu Ser Phe Tyr Lys Asn Glu Ile Cys Phe Gln Pro Asn
                 85                  90                  95

Gly Ala Leu Ile Glu Asp Ile Leu Gln Asn Trp Lys Asp Asn Tyr Asp
            100                 105                 110

Leu Leu Glu Glu Asn His Ser Tyr Ile Gln Trp Leu Phe Pro Leu Arg
        115                 120                 125

Glu Pro Gly Val Asn Trp His Ala Lys Pro Leu Thr Leu Lys Glu Val
130                 135                 140

Glu Ala Phe Lys Ser Ser Lys Glu Val Arg Glu Arg Leu Val Arg Ala
145                 150                 155                 160

Tyr Glu Leu Met Leu Gly Phe Tyr Gly Phe His Leu Glu Asp Arg Gly
                165                 170                 175

Thr Gly Ala Val Cys Arg Ala Gln Asn Phe Gln Pro Arg Phe His Asn
            180                 185                 190

Leu Asn Ser His Ser His Asn Asn Leu Arg Ile Thr Arg Ile Leu Lys
        195                 200                 205

Ser Leu Gly Glu Leu Gly Leu Glu His Tyr Gln Ala Pro Leu Val Arg
210                 215                 220

Phe Phe Leu Glu Glu Thr Leu Val Gln His Lys Leu Pro Ser Val Arg
225                 230                 235                 240

Gln Ser Ala Leu Asp Tyr Phe Leu Phe Ala Val Arg Cys Arg His Gln
                245                 250                 255

Arg Arg Glu Leu Val Tyr Phe Ala Trp Glu His Phe Lys Pro Arg Arg
            260                 265                 270

Glu Phe Val Trp Gly Pro Arg Asp Lys Leu Arg Arg Phe Lys Pro Gln
        275                 280                 285

Thr Ile Pro Gln Pro Leu Thr Gly Pro Gly Gln Ala Asp Lys Asp Glu
290                 295                 300

Gly Ser Arg Asp Pro Ser Gln Glu Ala Gly Thr Gln Gly Arg Thr Cys
305                 310                 315                 320

Gly Ser Gly Arg Asp Leu Ser Gly Asp Ser Gly Thr Ala Glu Asp Pro
                325                 330                 335
```

```
Ser Leu Leu Asn Thr Lys Pro Ser Asp Gly Gly Thr Leu Asp Gly Asn
            340                 345                 350

Gln Arg Asp Glu Ala Lys Ser Leu Ser Pro Lys Glu Ser Lys Lys Arg
        355                 360                 365

Lys Leu Glu Gly Asn Arg Gln Glu Gln Val Pro Gly Glu Ala Asp Pro
    370                 375                 380

Gln Gly Val Ser Glu Val Glu Lys Ile Ala Leu Asn Leu Glu Glu Cys
385                 390                 395                 400

Ala Leu Ser Pro Ile Ser Gln Glu Pro Arg Glu Ala Glu Pro Pro Cys
                405                 410                 415

Pro Val Ala Arg Val Ala Asn Glu Val Arg Lys Arg Lys Val Glu
            420                 425                 430

Glu Gly Ala Glu Gly Asp Gly Val Ser Asn Thr Gln Met Gln Ala
        435                 440                 445

Ser Ala Leu Pro Pro Thr Pro Ser Glu Cys Pro Glu Ala Gln Lys Asp
    450                 455                 460

Gly Asn Gly Pro Glu Asp Ser Asn Ser Gln Val Gly Ala Glu Asp Ser
465                 470                 475                 480

Lys Ser Gln Val Gly Pro Glu Asp Pro Asn Ser Gln Val Gly Leu Glu
                485                 490                 495

Asp Pro Asn Ser Gln Val Gly Pro Glu Asp Pro Asn Ser Gln Val Gly
            500                 505                 510

Pro Glu Asp Pro Asn Ser Gln Val Gly Pro Glu Asp Pro Asn Ser Gln
        515                 520                 525

Val Gly Pro Glu Asp Pro Asn Ser Gln Val Val Gly Pro Glu Gln Ala
    530                 535                 540

Ala Ser Lys Ser Pro Val Glu Asp Pro Asp Ser Asp Thr Met Gly Thr
545                 550                 555                 560

Ser Val Asp Glu Ser Glu Glu Leu Ala Arg Ile Glu Ala Ser Ala Glu
                565                 570                 575

Pro Pro Lys Pro
            580

<210> SEQ ID NO 3
<211> LENGTH: 987
<212> TYPE: DNA
<213> ORGANISM: Rattus norvegicus
<220> FEATURE:
<221> NAME/KEY: unsure
<222> LOCATION: (164)
<223> OTHER INFORMATION: n is unsure
<221> NAME/KEY: unsure
<222> LOCATION: (179)
<223> OTHER INFORMATION: n is unsure
<221> NAME/KEY: unsure
<222> LOCATION: (184)
<223> OTHER INFORMATION: n is unsure
<221> NAME/KEY: unsure
<222> LOCATION: (213)
<223> OTHER INFORMATION: n is unsure
<221> NAME/KEY: unsure
<222> LOCATION: (240)
<223> OTHER INFORMATION: n is unsure
<221> NAME/KEY: unsure
<222> LOCATION: (555)
<223> OTHER INFORMATION: n is unsure
<221> NAME/KEY: unsure
<222> LOCATION: (622)
<223> OTHER INFORMATION: n is unsure

<400> SEQUENCE: 3
```

```
cattgggccg acgtcgcatg ctcctctaga ctcgaggaat tcgggcccca gggtgtctct      60
gaggtagaga aaattgccct taaccttgag gagtgtgccc ttagccctat cagccaggag     120
cccagggagg stgaaccgcc ctgtcctgtg gccagggtgg ctanaatgag gtaagaaang    180
cggnaggaag gtggaggaag gggctgaggg tgnatggagt agtcagtaac actyaaatgn    240
caggccagtg ccctgcctcc taccccttca gagtgtcctg aggcccaaaa ggatgggaat    300
gggccagagg actcaaacag ccaggttggg gcagaggatt ccaaaagcca ggtggggccg    360
gaggatccaa acagccaggt ggggctggag gacccaaaca gccaggtcgg gccagaggac    420
ccaaacagcc aggtcgggcc agaggaccca aacagccagg tcgggccaga ggacccaaac    480
agccaggtcg ggccagagga cccaaacagc caggtggtgg ggccagagca agctgcctct    540
aagagccctg tggangggacc ctgactctga cactatggga acctcagtgg atgagtcaga    600
ggagttggca aggattgagg cntytgctga accccaaag ccttagaggt gcatttcagt     660
cctactcagc ccactgcagg gggtttctga gtccagagct ctgccgtagg ctcttcttgg    720
tgccccacag tgctggcctc tccctastgg tcactgaggt ggccaccaga gggactgagg    780
ccctgccctc agggaaggcc aaggccttca gaaccctcct tacctcactg tgtcctcctc    840
cactgccctc tgagccctgc gttgtgatca daccctaagg gtctagaggg aggggcctct    900
tcattagtct ggtgccaagt gaggccttt ctgaataaac tctttagact ttgtcaaaaa     960
aaaaaaaaaa aaaaaaaaa aaaaaaa                                          987

<210> SEQ ID NO 4
<211> LENGTH: 2290
<212> TYPE: DNA
<213> ORGANISM: Homo sapiens

<400> SEQUENCE: 4
tagaattcag cggccgctga attctagccg agcatggacg accccgactg cgactccacc      60
tgggaggagg acgaggagga tgcggaggac gcggaggacg aggactgcga ggacggcgag    120
gccgccggcg cgagggacgc ggacgcaggg gacgaggacg aggagtcgga ggagccgcgg    180
gcggcgcggc ccagctcgtt ccagtccaga atgacagggt ccagaaactg gcgagccacg    240
agggacatgt gtaggtatcg gcacaactat ccggatctgg tggaacgaga ctgcaatggg    300
gacacgccaa acctgagttt ctacagaaat gagatccgct tcctgcccaa cggctgtttc    360
attgaggaca ttcttcagaa ctggacggac aactatgacc tccttgagga caatcactcc    420
tacatccagt ggctgtgtttcc tctgcgagaa ccaggagtga actggcatgc caagcccctc    480
acgctcaggg aggtcgaggt gttttaaaagc tcccaggaga tccaggagcg gcttgtccgg    540
gcctacgagc tcatgctggg cttctacggg atccggctgg aggaccgagg cacgggcacg    600
gtgggccgag cacagaacta ccagaagcgc ttccagaacc tgaactggcg cagccacaac    660
aacctccgca tcacacgcat cctcaagtcg ccgtgtgagc tgagcctcga gcacttccag    720
gcgccactgg tccgcttctt cctggaggag acgctggtgc ggcgggagct gccgggggtg    780
cggcagagtg ccctggacta cttcatgttc gccgtgcgct gccgacacca cgccgccag     840
ctggtgcact cgcctggga gcacttccgg cccgctgca agttcgtctg ggggccccaa     900
gacaagctgc ggaggttcaa gcccagctct ctgccccatc cgctcgaggg ctccaggaag    960
gtggaggagg aaggaagccc cgggaccccc gaccacgagg ccagcaccca gggtcggacc    1020
tgtgggccag agcatagcaa gggtgggggc agggtggacg aggggcccca gccacgaggc    1080
gtggagcccc aggatgcggg acccctggag aggagccagg gggatgaggc aggggggccac    1140
```

-continued

```
ggggaagata ggccggagcc cttaagcccc aaagagagca agaagaggaa gctggagctg      1200
agccggcggg agcagccgcc cacagagcca ggccctcaga gtgcctcaga ggtggagaag      1260
atcgctctga atttggaggg gtgtgccctc agccagggca gcctcaggac ggggacccag      1320
gaagtgggcg gtcaggaccc tggggaggca gtgcagccct gccgccaacc cctgggagcc      1380
agggtggccg acaaggtgag gaagcggagg aaggtggatg aggtgctggg ggacagtgct      1440
gcggtggcca gtggtggtgc ccagaccttg gcccttgccg ggtcccctgc cccatcgggg      1500
caccccaagg ctggacacag tgagaacggg gttgaggagg acacagaagg tcgaacgggg      1560
cccaaagaag gtacccctgg gagcccatcg gagacccag gccccagccc agcaggacct      1620
gcaggggacg agccagccga gagcccatcg gagacccag gccccgccc ggcaggacct      1680 gcaggggacg agccagccga gagcccatcg gagacccag gccccagccc ggcaggacct      1740
acaagggatg agccagccga gagcccatcg gagacccag gccccgccc ggcaggacct      1800 gcaggggacg agccagccga gagcccatcg gagacccag gccccgccc ggcaggacct      1860 gcaggggacg agccagccga gagcccatcg gagacccag gccccagccc ggcaggacct      1920
acaagggatg agccagccaa ggcgggggag gcagcagagt tgcagkacgc agaggtggag      1980
tcttctgcca agtctgggaa gccttaagga aaggagtgcc cgtcggcgtc ttggtcctcc      2040
tgtccctgct gcaggggctg gggcctccgg agcttgctgc gggctcccct caggctctgc      2100
ttcgtgaccc gtgacccatg acccacagtg ctggcctcct gtgggccac tatagcarsc      2160 accagaagcc gcgaggccct cagggaagcc caaggcctgc agaagcctcc tggcctggct      2220
gtgtcttccc cacccagctc tccctgcgc ccctgtcttt gtaaattgac ccttctggag      2280
tgggggcgg                                                              2290
```

<210> SEQ ID NO 5
<211> LENGTH: 2408
<212> TYPE: DNA
<213> ORGANISM: Homo sapiens

<400> SEQUENCE: 5

```
tagaattcag cggccgctga attctagccg agcatggacg accccgactg cgactccacc        60
tgggaggagg acgaggagga tgcggaggac gcggaggacg aggactgcga ggacggcgag       120
gccgccggcg cgagggacgc ggacgcaggg gacgaggacg aggagtcgga ggagccgcgg       180
gcggcgcggc ccagctcgtt ccagtccaga atgacaggt ccagaaactg gcgagccacg       240
agggacatgt gtaggtatcg gcacaactat ccggatctgg tggaacgaga ctgcaatggg       300
gacacgccaa acctgagttt ctacagaaat gagatccgct tcctgcccaa cggctgtttc       360
attgaggaca ttcttcagaa ctggacggac aactatgacc tccttgagga caatcactcc       420
tacatccagt ggctgtttcc tctgcgagaa ccaggagtga actggcatgc caagcccctc       480
acgctcaggg aggtcgaggt gttttaaaagc tcccaggaga tccaggagcg gcttgtccgg       540
gcctacgagc tcatgctggg cttctacggg atccggctgg aggaccgagg cacgggcacg       600
gtgggccgag cacagaacta ccagaagcgc ttccagaacc tgaactggcg cagccacaac       660
aacctccgca tcacacgcat cctcaagtcg ccgtgtgagc tgagcctcga gcacttccag       720
gcgccactgg tccgcttctt cctggaggag acgctggtgc ggcgggagct gccggggggtg       780 cggcagagtg ccctggacta cttcatgttc gccgtgcgct gccgacacca gcgccgccag       840
ctggtgcact tcgcctggga gcacttccgg ccccgctgca agttcgtctg ggggcccaa        900
```

-continued

```
gacaagctgc ggaggttcaa gcccagctct ctgccgcatc cgctcgaggg ctccaggaag      960
gtggaggagg aaggaagccc cggggacccc gaccacgagg ccagcaccca gggtcggacc     1020
tgtgagccag agcatagcaa gggtgggggc agggtggacg aggggcccca gccacggagc     1080
gtggagcccc aggatgcggg acccctggag aggagccagg gggatgaggc agggggccac     1140
ggggaagata ggccggagcc cttaagcccc aaagagagca agaagaggaa gctggagctg     1200
agccggcggg agcagccgcc cacagggcca ggccctcaga gtgcctcaga ggtggagaag     1260
atcgctctga atttggaggg gtgtgccctc agccagggca gcctcaggac ggggacccag     1320
gaagtgggcg gtcaggaccc tggggaggca gtgcagccct gccgccaacc cctgggagcc     1380
agggtggccg acaaggtgag gaagcggagg aaggtggatg agggtactgg ggacagtgct     1440
gcggtggcca gtggtggtgc ccagaccttg gcccttgccg ggtcccctgc ccatcggggg     1500
caccccaagg ctggacacag tgagaacggg gttgaggagg acacagaagg tcgaacgggg     1560
cccaaagaag gtaccctggg gagcccatcg gagacccccag gccccagccc agcaggacct     1620
gcagggggacg agccagccaa gacccccatcg gagacccccag gccccagccc ggcaggacct     1680
acaagggatg agccagccga gagcccatcg gagacccccag gccccgcccc ggcaggacct     1740
gcagggggacg agccagccga gagcccatcg gagacccccag gccccgcccc ggcaggacct     1800
gcagggggacg agccagccaa gatcccatcg gagacccccag gccccagccc ggcaggacct     1860
acaagggatg agccagccga gagcccatcg gagacccccag gccccgcccc ggcaggacct     1920
gcagggggacg agccagccga gagcccatcg gagacccccag gccccgcccc ggcaggacct     1980
gcagggggacg agccagccga gagcccatcg gagacccccag gccccagccc ggcaggacct     2040
acaagggatg agccagccaa ggcgggggag gcagcagagt tgcaggacgc agaggtggag     2100
tcttctgcca agtctgggaa gccttaagga aaggagtgcc cgtcggcgtc ttggtcctcc     2160
tgtccctgct gcaggggctg gggcctccgg agctgctgcg ggctcccctc aggctctgct     2220
tcgtgacccg tgacccatga cccacagtgc tggcctcctg tggggccact atagcagcca     2280
ccagaagccg cgaggccctc agggaagccc aaggcctgca gaagcctcct ggcctggctg     2340
tgtcttcccc acccagctct ccctgcgcc cctgtctttg taaattgacc cttctggagt     2400
gggggggcg                                                            2408
```

<210> SEQ ID NO 6
<211> LENGTH: 697
<212> TYPE: PRT
<213> ORGANISM: Homo sapiens

<400> SEQUENCE: 6

Met Asp Asp Pro Asp Cys Asp Ser Thr Trp Glu Glu Asp Glu Glu Asp
1               5                   10                  15

Ala Glu Asp Ala Glu Asp Glu Asp Cys Glu Asp Gly Glu Ala Ala Gly
                20                  25                  30

Ala Arg Asp Ala Asp Ala Gly Asp Glu Asp Glu Glu Ser Glu Glu Pro
            35                  40                  45

Arg Ala Ala Arg Pro Ser Ser Phe Gln Ser Arg Met Thr Gly Ser Arg
        50                  55                  60

Asn Trp Arg Ala Thr Arg Asp Met Cys Arg Tyr Arg His Asn Tyr Pro
65                  70                  75                  80

Asp Leu Val Glu Arg Asp Cys Asn Gly Asp Thr Pro Asn Leu Ser Phe
                85                  90                  95

Tyr Arg Asn Glu Ile Arg Phe Leu Pro Asn Gly Cys Phe Ile Glu Asp

-continued

```
                100                 105                 110
Ile Leu Gln Asn Trp Thr Asp Asn Tyr Asp Leu Leu Glu Asp Asn His
            115                 120                 125
Ser Tyr Ile Gln Trp Leu Phe Pro Leu Arg Glu Pro Gly Val Asn Trp
        130                 135                 140
His Ala Lys Pro Leu Thr Leu Arg Glu Val Glu Val Phe Lys Ser Ser
145                 150                 155                 160
Gln Glu Ile Gln Glu Arg Leu Val Arg Ala Tyr Glu Leu Met Leu Gly
                165                 170                 175
Phe Tyr Gly Ile Arg Leu Glu Asp Arg Gly Thr Gly Thr Val Gly Arg
            180                 185                 190
Ala Gln Asn Tyr Gln Lys Arg Phe Gln Asn Leu Asn Trp Arg Ser His
        195                 200                 205
Asn Asn Leu Arg Ile Thr Arg Ile Leu Lys Ser Pro Cys Glu Leu Ser
210                 215                 220
Leu Glu His Phe Gln Ala Pro Leu Val Arg Phe Phe Leu Glu Glu Thr
225                 230                 235                 240
Leu Val Arg Arg Glu Leu Pro Gly Val Arg Gln Ser Ala Leu Asp Tyr
                245                 250                 255
Phe Met Phe Ala Val Arg Cys Arg His Gln Arg Arg Gln Leu Val His
            260                 265                 270
Phe Ala Trp Glu His Phe Arg Pro Arg Cys Lys Phe Val Trp Gly Pro
        275                 280                 285
Gln Asp Lys Leu Arg Arg Phe Lys Pro Ser Ser Leu Pro His Pro Leu
    290                 295                 300
Glu Gly Ser Arg Lys Val Glu Glu Gly Ser Pro Gly Asp Pro Asp
305                 310                 315                 320
His Glu Ala Ser Thr Gln Gly Arg Thr Cys Glu Pro Glu His Ser Lys
                325                 330                 335
Gly Gly Gly Arg Val Asp Glu Gly Pro Gln Pro Arg Ser Val Glu Pro
            340                 345                 350
Gln Asp Ala Gly Pro Leu Glu Arg Ser Gln Gly Asp Glu Ala Gly Gly
        355                 360                 365
His Gly Glu Asp Arg Pro Glu Pro Leu Ser Pro Lys Glu Ser Lys Lys
    370                 375                 380
Arg Lys Leu Glu Leu Ser Arg Arg Glu Gln Pro Pro Thr Gly Pro Gly
385                 390                 395                 400
Pro Gln Ser Ala Ser Glu Val Glu Lys Ile Ala Leu Asn Leu Glu Gly
                405                 410                 415
Cys Ala Leu Ser Gln Gly Ser Leu Arg Thr Gly Thr Gln Glu Val Gly
            420                 425                 430
Gly Gln Asp Pro Gly Glu Ala Val Gln Pro Cys Arg Gln Pro Leu Gly
        435                 440                 445
Ala Arg Val Ala Asp Lys Val Arg Lys Arg Lys Val Asp Glu Gly
    450                 455                 460
Thr Gly Asp Ser Ala Ala Val Ala Ser Gly Ala Gln Thr Leu Ala
465                 470                 475                 480
Leu Ala Gly Ser Pro Ala Pro Ser Gly His Pro Lys Ala Gly His Ser
                485                 490                 495
Glu Asn Gly Val Glu Glu Asp Thr Glu Gly Arg Thr Gly Pro Lys Glu
            500                 505                 510
Gly Thr Pro Gly Ser Pro Ser Glu Thr Pro Gly Pro Ser Pro Ala Gly
        515                 520                 525
```

```
Pro Ala Gly Asp Glu Pro Ala Lys Thr Pro Ser Glu Thr Pro Gly Pro
    530                 535                 540

Ser Pro Ala Gly Pro Thr Arg Asp Glu Pro Ala Glu Ser Pro Ser Glu
545                 550                 555                 560

Thr Pro Gly Pro Arg Pro Ala Gly Pro Ala Gly Asp Glu Pro Ala Glu
                565                 570                 575

Ser Pro Ser Glu Thr Pro Gly Pro Arg Pro Ala Gly Pro Ala Gly Asp
            580                 585                 590

Glu Pro Ala Lys Ile Pro Ser Glu Thr Pro Gly Pro Ser Pro Ala Gly
            595                 600                 605

Pro Thr Arg Asp Glu Pro Ala Glu Ser Pro Ser Glu Thr Pro Gly Pro
    610                 615                 620

Arg Pro Ala Gly Pro Ala Gly Asp Glu Pro Ala Glu Ser Pro Ser Glu
625                 630                 635                 640

Thr Pro Gly Pro Arg Pro Ala Gly Pro Ala Gly Asp Glu Pro Ala Glu
                645                 650                 655

Ser Pro Ser Glu Thr Pro Gly Pro Ser Pro Ala Gly Pro Thr Arg Asp
            660                 665                 670

Glu Pro Ala Lys Ala Gly Glu Ala Ala Glu Leu Gln Asp Ala Glu Val
    675                 680                 685

Glu Ser Ser Ala Lys Ser Gly Lys Pro
    690                 695

<210> SEQ ID NO 7
<211> LENGTH: 1601
<212> TYPE: DNA
<213> ORGANISM: Homo sapiens

<400> SEQUENCE: 7
tagaattcag cggccgctga attctagccg agcatggacg accccgactg cgactccacc      60
tgggaggagg acgaggagga tgcggaggac gcggaggacg aggactgcga ggacggcgag     120
gccgccggcg cgagggacgc ggacgcaggg gacgaggacg aggagtcgga ggagccgcgg     180
gcggcgcggc ccagctcgtt ccagtccaga atgacagggt ccagaaactg gcgagccacg     240
agggacatgt gtaggtatcg cacaactat ccggatctgg tggaacgaga ctgcaatggg      300
gacacgccaa acctgagttt ctacagaaat gagatccgct tcctgcccaa cggctgtttc     360
attgaggaca tcttcagaa ctggacggac aactatgacc tccttgagga caatcactcc      420
tacatccagt ggctgttttcc tctgcgagaa ccaggagtga actggcatgc caagcccctc     480
acgctcaggg aggtcgaggt gttaaaagc tcccaggaga tccaggagcg gcttgtccgg      540
gcctacgagc tcatgctggg cttctacggg atccggctgg aggaccgagg cacgggcacg     600
gtgggccgag cacagaacta ccagaagcgc ttccagaacc tgaactggcg cagccacaac     660
aacctccgca tcacacgcat cctcaagtcg ccgtgtgagc tgagcctcga gcacttccag     720
gcgccactgg tccgcttctt cctggaggag cgctggtgc ggcgggagct gccggggtg      780 cggcagagtg ccctggacta cttcatgttc gccgtgcgct ccgacacca cgccgccag      840 ctggtgcact cgcctgggga gcacttccgg cccgctgca agttcgtctg ggggccccaa      900
gacaagctgc ggaggttcaa gcccagctct ctgccgcatc cgctcgaggg ctccaggaag     960
gtggaggagg aaggaagccc cggggacccc gaccacgagg ccagcaccca gggtcggacc    1020
tgtgggccag agcatagcaa gggtgggggc agggtggacg aggggcccca gccacgagc     1080 gtggagcccc aggatgcggg acccctggag aggagccagg gggatgaggc aggggggccac    1140
```

```
ggggaagata ggccggagcc cttaagcccc aaagagagca agaagaggaa gctggagctg    1200
agccggcggg agcagccgcc cacagagcca ggccctcaga gtgcctcaga ggtggagaag    1260
atcgctctga atttggaggg gtgtgccctc agccagggca gcctcaggac ggggacccag    1320
gaagtgggcg gtcaggaccc tggggaggcc tcctgtccct gctgcagggg ctggggcctc    1380
cggagctgct gcgggctccc ctcaggctct gcttcgtgac ccgtgaccca tgacccacag    1440
tgctggcctc ctgtggggcc actatagcag ccaccagaag ccgcgaggcc ctcagggaag    1500
cccaaggcct gcaggagcct cctggcctgg ctgtgtcttc cccacccagc tctcccctgc    1560
gcccctgtct ttgtaaattg accttctgg agtggggggc g                         1601
```

<210> SEQ ID NO 8
<211> LENGTH: 461
<212> TYPE: PRT
<213> ORGANISM: Homo sapiens

<400> SEQUENCE: 8

```
Met Asp Asp Pro Asp Cys Asp Ser Thr Trp Glu Glu Asp Glu Glu Asp
 1               5                  10                  15

Ala Glu Asp Ala Glu Asp Glu Asp Cys Glu Asp Gly Glu Ala Ala Gly
             20                  25                  30

Ala Arg Asp Ala Asp Ala Gly Asp Glu Asp Glu Glu Ser Glu Glu Pro
         35                  40                  45

Arg Ala Ala Arg Pro Ser Ser Phe Gln Ser Arg Met Thr Gly Ser Arg
     50                  55                  60

Asn Trp Arg Ala Thr Arg Asp Met Cys Arg Tyr Arg His Asn Tyr Pro
 65                  70                  75                  80

Asp Leu Val Glu Arg Asp Cys Asn Gly Asp Thr Pro Asn Leu Ser Phe
                 85                  90                  95

Tyr Arg Asn Glu Ile Arg Phe Leu Pro Asn Gly Cys Phe Ile Glu Asp
            100                 105                 110

Ile Leu Gln Asn Trp Thr Asp Asn Tyr Asp Leu Leu Glu Asp Asn His
        115                 120                 125

Ser Tyr Ile Gln Trp Leu Phe Pro Leu Arg Glu Pro Gly Val Asn Trp
    130                 135                 140

His Ala Lys Pro Leu Thr Leu Arg Glu Val Glu Val Phe Lys Ser Ser
145                 150                 155                 160

Gln Glu Ile Gln Glu Arg Leu Val Arg Ala Tyr Glu Leu Met Leu Gly
                165                 170                 175

Phe Tyr Gly Ile Arg Leu Glu Asp Arg Gly Thr Gly Thr Val Gly Arg
            180                 185                 190

Ala Gln Asn Tyr Gln Lys Arg Phe Gln Asn Leu Asn Trp Arg Ser His
        195                 200                 205

Asn Asn Leu Arg Ile Thr Arg Ile Leu Lys Ser Pro Cys Glu Leu Ser
    210                 215                 220

Leu Glu His Phe Gln Ala Pro Leu Val Arg Phe Leu Glu Glu Thr
225                 230                 235                 240

Leu Val Arg Arg Glu Leu Pro Gly Val Arg Gln Ser Ala Leu Asp Tyr
                245                 250                 255

Phe Met Phe Ala Val Arg Cys Arg His Gln Arg Gln Leu Val His
            260                 265                 270

Phe Ala Trp Glu His Phe Arg Pro Arg Cys Lys Phe Val Trp Gly Pro
        275                 280                 285
```

-continued

```
Gln Asp Lys Leu Arg Arg Phe Lys Pro Ser Ser Leu Pro His Pro Leu
    290                 295                 300
Glu Gly Ser Arg Lys Val Glu Glu Gly Ser Pro Gly Asp Pro Asp
305                 310                 315                 320
His Glu Ala Ser Thr Gln Gly Arg Thr Cys Gly Pro Glu His Ser Lys
                325                 330                 335
Gly Gly Gly Arg Val Asp Glu Gly Pro Gln Pro Arg Ser Val Glu Pro
            340                 345                 350
Gln Asp Ala Gly Pro Leu Glu Arg Ser Gln Gly Asp Glu Ala Gly Gly
        355                 360                 365
His Gly Glu Asp Arg Pro Glu Pro Leu Ser Pro Lys Glu Ser Lys Lys
    370                 375                 380
Arg Lys Leu Glu Leu Ser Arg Arg Glu Gln Pro Pro Thr Glu Pro Gly
385                 390                 395                 400
Pro Gln Ser Ala Ser Glu Val Glu Lys Ile Ala Leu Asn Leu Glu Gly
                405                 410                 415
Cys Ala Leu Ser Gln Gly Ser Leu Arg Thr Gly Thr Gln Glu Val Gly
            420                 425                 430
Gly Gln Asp Pro Gly Glu Ala Ser Cys Pro Cys Cys Arg Gly Trp Gly
        435                 440                 445
Leu Arg Ser Cys Cys Gly Leu Pro Ser Gly Ser Ala Ser
    450                 455                 460
```

<210> SEQ ID NO 9
<211> LENGTH: 2348
<212> TYPE: DNA
<213> ORGANISM: Homo sapiens

<400> SEQUENCE: 9

| | | | | | | |
|---|---|---|---|---|---|---|
| tagaattcag | cggccgctga | attctagccg | agcatggacg | accccgactg | cgactccacc | 60 |
| tgggaggagg | acgaggagga | tgcggaggac | gcggaggacg | aggactgcga | ggacggcgag | 120 |
| gccgccggcg | cgagggacgc | ggacgcaggg | gacgaggacg | aggagtcgga | ggagccgcgg | 180 |
| gcggcgcggc | ccagctcgtt | ccagtccaga | atgacagggt | ccagaaactg | cgagccacg | 240 |
| agggacatgt | gtaggtatcg | gcacaactat | ccggatctgg | tggaacgaga | ctgcaatggg | 300 |
| gacacgccaa | acctgagttt | ctacagaaat | gagatccgct | tcctgcccaa | cggctgtttc | 360 |
| attgaggaca | ttcttcagaa | ctggacggac | aactatgacc | tccttgagga | caatcactcc | 420 |
| tacatccagt | ggctgttttcc | tctgcgagaa | ccaggagtga | actggcatgc | caagcccctc | 480 |
| acgctcaggg | aggtcgaggt | gtttaaaagc | tcccaggaga | tccaggagcg | gcttgtccgg | 540 |
| gcctacgagc | tcatgctggg | cttctacggg | atccggctgg | aggaccgagg | cacgggcacg | 600 |
| gtgggccgag | cacagaacta | ccagaagcgc | ttccagaacc | tgaactggcg | cagccacaac | 660 |
| aacctccgca | tcacacgcat | cctcaagtcg | ccgtgtgagc | tgagcctcga | gcacttccag | 720 |
| gcgccactgg | tccgcttctt | cctggaggag | acgctggtgc | ggcgggagct | gccggggggtg | 780 |
| cggcagagtg | ccctggacta | cttcatgttc | gccgtcgcct | ccgacacca | gcgccgccag | 840 |
| ctggtgcact | cgcctggga | gcacttccgg | ccccgctgca | agttcgtctg | ggggccccaa | 900 |
| gacaagctgc | ggaggttcaa | gcccagctct | ctgccgcatc | cgctcgaggg | ctccaggaag | 960 |
| gtggaggagg | aaggaagccc | cggggacccc | gaccacgagg | ccagcaccca | gggtcggacc | 1020 |
| tgtgggccag | agcatagcaa | gggtgggggc | agggtggacg | aggggccccca | gccacggagc | 1080 |
| gtggagcccc | aggatgcggg | accctgagg | aggagccagg | gggatgaggc | aggggggccac | 1140 |

-continued

```
gggaagata ggccggagcc cttaagcccc aaagagagca agaagaggaa gctggagctg      1200
agccggcggg agcagccgcc cacagagcca ggccctcaga gtgcctcaga ggtggagaag      1260
atcgctctga atttggaggg gtgtgccctc agccagggca gcctcaggac ggggacccag      1320
gaagtgggcg gtcaggaccc tggggaggca gtgcagccct gccgccaacc cctgggagcc      1380
agggtggccg acaaggtgag gaagcggagg aaggtggatg aggtgctggg ggacagtgct      1440
gcggtggcca gtggtggtgc ccagaccttg gcccttgccg ggtcccctgc cccatcgggg      1500
caccccaagg ctggacacag tgagaacggg gttgaggagg acacagaagg tcgaacgggg      1560
cccaaagaag gtaccctggg gagcccatcg gagacccccag gccccagccc agcaggacct      1620 gcagggacg agccagccga gagcccatcg gagacccccag gccccgccc agcaggacct      1680 gcagggacg agccagccga gagcccatcg gagacccccag gcctccgccc ggcaggacct      1740 gcagggacg agccagccga gacccccatcg gagacccccag gccccagccc ggcaggacct      1800
acaagggatg agccagccga gagcccatcg gagacccccag gccccgccc ggcaggacct      1860 gcagggacg agccagccga gagcccatcg gagacccccag gccccgccc ggcaggacct      1920 gcagggacg aaccagccga gagcccatcg gagacccccag gccccagccc ggcaggacct      1980
acaagggatg agccagccaa ggcgggggag gcagcagagt tgcaggacgc agaggtggag      2040
tcttctgcca agtctgggaa gccttaagga aaggagtgcc cgtcggcgtc ttggtcctcc      2100
tgtccctgct gcaggggctg gggcctccgg agctgctgcg gactcccctc aggctctgct      2160
tcgtgacccg tgacccatga cccacagtgc tggcctcctg tggggccact atagcagcca      2220
ccagaagccg cgaggccctc agggaagccc aaggcctgca gaagcctcct ggcctggctg      2280
tgtcttcccc acccagctct cccctgcgcc cctgtctttg taaattgacc cttctggagt      2340
ggggggcg                                                              2348
```

<210> SEQ ID NO 10
<211> LENGTH: 677
<212> TYPE: PRT
<213> ORGANISM: Homo sapiens

<400> SEQUENCE: 10

```
Met Asp Asp Pro Asp Cys Asp Ser Thr Trp Glu Glu Asp Glu Glu Asp
 1               5                  10                  15

Ala Glu Asp Ala Glu Asp Glu Asp Cys Glu Asp Gly Glu Ala Ala Gly
                20                  25                  30

Ala Arg Asp Ala Asp Ala Gly Asp Glu Asp Glu Glu Ser Glu Glu Pro
         35                  40                  45

Arg Ala Ala Arg Pro Ser Ser Phe Gln Ser Arg Met Thr Gly Ser Arg
     50                  55                  60

Asn Trp Arg Ala Thr Arg Asp Met Cys Arg Tyr Arg His Asn Tyr Pro
 65                  70                  75                  80

Asp Leu Val Glu Arg Asp Cys Asn Gly Asp Thr Pro Asn Leu Ser Phe
                 85                  90                  95

Tyr Arg Asn Glu Ile Arg Phe Leu Pro Asn Gly Cys Phe Ile Glu Asp
                100                 105                 110

Ile Leu Gln Asn Trp Thr Asp Asn Tyr Asp Leu Leu Glu Asp Asn His
         115                 120                 125

Ser Tyr Ile Gln Trp Leu Phe Pro Leu Arg Glu Pro Gly Val Asn Trp
     130                 135                 140

His Ala Lys Pro Leu Thr Leu Arg Glu Val Glu Val Phe Lys Ser Ser
145                 150                 155                 160
```

```
Gln Glu Ile Gln Glu Arg Leu Val Arg Ala Tyr Glu Leu Met Leu Gly
                165                 170                 175
Phe Tyr Gly Ile Arg Leu Glu Asp Arg Gly Thr Gly Thr Val Gly Arg
            180                 185                 190
Ala Gln Asn Tyr Gln Lys Arg Phe Gln Asn Leu Asn Trp Arg Ser His
        195                 200                 205
Asn Asn Leu Arg Ile Thr Arg Ile Leu Lys Ser Pro Cys Glu Leu Ser
    210                 215                 220
Leu Glu His Phe Gln Ala Pro Leu Val Arg Phe Phe Leu Glu Glu Thr
225                 230                 235                 240
Leu Val Arg Arg Glu Leu Pro Gly Val Arg Gln Ser Ala Leu Asp Tyr
                245                 250                 255
Phe Met Phe Ala Val Arg Cys Arg His Gln Arg Arg Gln Leu Val His
            260                 265                 270
Phe Ala Trp Glu His Phe Arg Pro Arg Cys Lys Phe Val Trp Gly Pro
        275                 280                 285
Gln Asp Lys Leu Arg Arg Phe Lys Pro Ser Ser Leu Pro His Pro Leu
    290                 295                 300
Glu Gly Ser Arg Lys Val Glu Glu Gly Ser Pro Gly Asp Pro Asp
305                 310                 315                 320
His Glu Ala Ser Thr Gln Gly Arg Thr Cys Gly Pro Glu His Ser Lys
                325                 330                 335
Gly Gly Gly Arg Val Asp Glu Gly Pro Gln Pro Arg Ser Val Glu Pro
            340                 345                 350
Gln Asp Ala Gly Pro Leu Glu Arg Ser Gln Gly Asp Glu Ala Gly Gly
        355                 360                 365
His Gly Glu Asp Arg Pro Glu Pro Leu Ser Pro Lys Glu Ser Lys Lys
    370                 375                 380
Arg Lys Leu Glu Leu Ser Arg Arg Glu Gln Pro Pro Thr Glu Pro Gly
385                 390                 395                 400
Pro Gln Ser Ala Ser Glu Val Glu Lys Ile Ala Leu Asn Leu Glu Gly
                405                 410                 415
Cys Ala Leu Ser Gln Gly Ser Leu Arg Thr Gly Thr Gln Glu Val Gly
            420                 425                 430
Gly Gln Asp Pro Gly Glu Ala Val Gln Pro Cys Arg Gln Pro Leu Gly
        435                 440                 445
Ala Arg Val Ala Asp Lys Val Arg Lys Arg Lys Val Asp Glu Gly
450                 455                 460
Ala Gly Asp Ser Ala Ala Val Ala Ser Gly Gly Ala Gln Thr Leu Ala
465                 470                 475                 480
Leu Ala Gly Ser Pro Ala Pro Ser Gly His Pro Lys Ala Gly His Ser
                485                 490                 495
Glu Asn Gly Val Glu Glu Asp Thr Glu Gly Arg Thr Gly Pro Lys Glu
            500                 505                 510
Gly Thr Pro Gly Ser Pro Ser Glu Thr Pro Gly Pro Ser Pro Ala Gly
        515                 520                 525
Pro Ala Gly Asp Glu Pro Ala Glu Ser Pro Ser Glu Thr Pro Gly Pro
    530                 535                 540
Arg Pro Ala Gly Pro Ala Gly Asp Glu Pro Ala Glu Ser Pro Ser Glu
545                 550                 555                 560
Thr Pro Gly Leu Arg Pro Ala Gly Pro Ala Gly Asp Glu Pro Ala Glu
                565                 570                 575
```

```
Thr Pro Ser Glu Thr Pro Gly Pro Ser Pro Ala Gly Pro Thr Arg Asp
            580                 585                 590

Glu Pro Ala Glu Ser Pro Ser Glu Thr Pro Gly Pro Arg Pro Ala Gly
            595                 600                 605

Pro Ala Gly Asp Glu Pro Ala Glu Ser Pro Ser Glu Thr Pro Gly Pro
            610                 615                 620

Arg Pro Ala Gly Pro Ala Gly Asp Glu Pro Ala Glu Ser Pro Ser Glu
625                 630                 635                 640

Thr Pro Gly Pro Ser Pro Ala Gly Pro Thr Arg Asp Glu Pro Ala Lys
            645                 650                 655

Ala Gly Glu Ala Ala Glu Leu Gln Asp Ala Glu Val Glu Ser Ser Ala
            660                 665                 670

Lys Ser Gly Lys Pro
            675

<210> SEQ ID NO 11
<211> LENGTH: 2289
<212> TYPE: DNA
<213> ORGANISM: Homo sapiens

<400> SEQUENCE: 11
tagaattcag cggccgctga attctagccg agcatggacg accccgactg cgactccacc        60
tgggaggagg acgaggagga tgcggaggac gcggaggacg aggactgcga ggacggcgag       120
gccgccggcg cgagggacgc ggacgcaggg gacgaggacg aggagtcgga ggagccgcgg       180
gcggcgcggc ccagctcgtt ccagtccaga atgacagggt ccagaaactg cgagccacg        240 agggacatgt gtaggtatcg cacaactat ccggatctgg tggaacgaga ctgcaatggg        300
gacacgccaa acctgagttt ctacagaaat gagatccgct tcctgcccaa cggctgtttc       360
attgaggaca ttcttcagaa ctggacggac aactatgacc tccttgagga caatcactcc       420
tacatccagt ggctgtttcc tctgcgagaa ccaggagtga actggcatgc aagcccctc        480 acgctcaggg aggtcgaggt gttttaaaagc tcccaggaga tccaggagcg gcttgtccgg      540
gcctacgagc tcatgctggg cttctacggg atccggctgg aggaccgagg cacgggcacg      600
gtgggccgag cacagaacta ccagaagcgc ttccagaacc tgaactggcg cagccacaac      660
aacctccgca tcacacgcat cctcaagtcg ccgtgtgagc tgagcctcga gcacttccag      720
gcgccactgg tccgcttctt cctggaggag acgctggtgc ggcgggagct gccggggtg       780 cggcagagtg ccctggacta cttcatgttc gccgtgcgct ccgacacca gcgccgccag       840 ctggtgcact cgcctggga gcacttccgg ccccgctgca gttcgtctg ggggccccaa        900 gacaagctgc ggaggttcaa gcccagctct ctgccccatc cgctcgaggg ctccaggaag      960
gtggaggagg aaggaagccc cggggacccc gaccacgagg ccagcaccca gggtcggacc     1020
tgtgggccag agcatagcaa gggtgggggc agggtggacg aggggcccca gccacggagc     1080
gtggagcccc aggatgcggg acccctggag aggagccagg gggatgaggc aggggggccac    1140 gggaaagata ggccggagcc cttaagcccc aaagagagca agaagaggaa gctggagctg     1200
agccggcggg agcagccgcc cacagagcca ggccctcaga gtgcctcaga ggtggagaag     1260
atcgctctga atttggaggg gtgtgccctc agccagggca gcctcaggac ggggacccag     1320
gaagtgggcg tcaggaccc tggggaggca gtgcagccct gccgccaacc cctgggagcc     1380
agggtggccg acaaggtgag gaagcggagg aaggtggatg agggtgctgg ggacagtgct    1440
gcggtggcca gtggtggtgc ccagaccttg gcccttgccg ggtcccctgc cccatcgggg    1500
```

| | | |
|---|---|---|
| caccccaagg ctggacacag tgagaacggg gttgaggagg acacagaagg tcgaacgggg | 1560 | |
| cccaaagaag gtaccoctgg gagcccatcg gagaccccag gccccagccc agcaggacct | 1620 | |
| gcagggacg agccagccga gagcccatcg gagaccccag gccccgccc ggcaggacct | 1680 | |
| gcagggacg agccagccga gagcccatcg gagaccccag gccccagccc ggcaggacct | 1740 | |
| acaagggatg agccagccga gagcccatcg gagaccccag gccccgccc ggcaggacct | 1800 | |
| gcagggacg agccagccga gagcccatcg gagaccccag gccccgccc ggcaggacct | 1860 | |
| gcagggacg agccagccga gagcccatcg gagaccccag gccccagccc ggcaggacct | 1920 | |
| acaagggatg agccagccaa ggcgggggag gcagcagagt tgcaggacgc agaggtggag | 1980 | |
| tcttctgcca agtctgggaa gccttaagga aaggagtgcc cgtcggcgtc ttggtcctcc | 2040 | |
| tgtccctgct gcaggggctg gggcctccgg agctgctgcg ggctcccctc aggctctgct | 2100 | |
| tcgtgacccg tgacccatga cccacagtgc tggcctcctg tggggccact atagcagcca | 2160 | |
| ccagaagccg cgaggccctc agggaagccc aaggcctgca gaagcctcct ggcctggctg | 2220 | |
| tgtcttcccc acccagctct cccctgcgcc cctgtctttg taaattgacc cttctggagt | 2280 | |
| gggggcgg | 2289 | |

<210> SEQ ID NO 12
<211> LENGTH: 657
<212> TYPE: PRT
<213> ORGANISM: Homo sapiens

<400> SEQUENCE: 12

```
Met Asp Asp Pro Asp Cys Asp Ser Thr Trp Glu Glu Asp Glu Glu Asp
 1               5                  10                  15

Ala Glu Asp Ala Glu Asp Glu Asp Cys Glu Asp Gly Glu Ala Ala Gly
                20                  25                  30

Ala Arg Asp Ala Asp Ala Gly Asp Glu Asp Glu Glu Ser Glu Glu Pro
            35                  40                  45

Arg Ala Ala Arg Pro Ser Ser Phe Gln Ser Arg Met Thr Gly Ser Arg
        50                  55                  60

Asn Trp Arg Ala Thr Arg Asp Met Cys Arg Tyr Arg His Asn Tyr Pro
 65                  70                  75                  80

Asp Leu Val Glu Arg Asp Cys Asn Gly Asp Thr Pro Asn Leu Ser Phe
                 85                  90                  95

Tyr Arg Asn Glu Ile Arg Phe Leu Pro Asn Gly Cys Phe Ile Glu Asp
                100                 105                 110

Ile Leu Gln Asn Trp Thr Asp Asn Tyr Asp Leu Leu Glu Asp Asn His
            115                 120                 125

Ser Tyr Ile Gln Trp Leu Phe Pro Leu Arg Glu Pro Gly Val Asn Trp
        130                 135                 140

His Ala Lys Pro Leu Thr Leu Arg Glu Val Glu Val Phe Lys Ser Ser
145                 150                 155                 160

Gln Glu Ile Gln Glu Arg Leu Val Arg Ala Tyr Glu Leu Met Leu Gly
                165                 170                 175

Phe Tyr Gly Ile Arg Leu Glu Asp Arg Gly Thr Gly Thr Val Gly Arg
                180                 185                 190

Ala Gln Asn Tyr Gln Lys Arg Phe Gln Asn Leu Asn Trp Arg Ser His
            195                 200                 205

Asn Asn Leu Arg Ile Thr Arg Ile Leu Lys Ser Pro Cys Glu Leu Ser
        210                 215                 220

Leu Glu His Phe Gln Ala Pro Leu Val Arg Phe Phe Leu Glu Glu Thr
```

-continued

```
                225                 230                 235                 240
Leu Val Arg Arg Glu Leu Pro Gly Val Arg Gln Ser Ala Leu Asp Tyr
                    245                 250                 255
Phe Met Phe Ala Val Arg Cys Arg His Gln Arg Arg Gln Leu Val His
                260                 265                 270
Phe Ala Trp Glu His Phe Arg Pro Arg Cys Lys Phe Val Trp Gly Pro
            275                 280                 285
Gln Asp Lys Leu Arg Arg Phe Lys Pro Ser Ser Leu Pro His Pro Leu
        290                 295                 300
Glu Gly Ser Arg Lys Val Glu Glu Gly Ser Pro Gly Asp Pro Asp
305                 310                 315                 320
His Glu Ala Ser Thr Gln Gly Arg Thr Cys Gly Pro Glu His Ser Lys
                325                 330                 335
Gly Gly Gly Arg Val Asp Glu Gly Pro Gln Pro Arg Ser Val Glu Pro
                340                 345                 350
Gln Asp Ala Gly Pro Leu Glu Arg Ser Gln Gly Asp Glu Ala Gly Gly
            355                 360                 365
His Gly Glu Asp Arg Pro Glu Pro Leu Ser Pro Lys Glu Ser Lys Lys
        370                 375                 380
Arg Lys Leu Glu Leu Ser Arg Arg Glu Gln Pro Pro Thr Glu Pro Gly
385                 390                 395                 400
Pro Gln Ser Ala Ser Glu Val Glu Lys Ile Ala Leu Asn Leu Glu Gly
                405                 410                 415
Cys Ala Leu Ser Gln Gly Ser Leu Arg Thr Gly Thr Gln Glu Val Gly
                420                 425                 430
Gly Gln Asp Pro Gly Glu Ala Val Gln Pro Cys Arg Gln Pro Leu Gly
            435                 440                 445
Ala Arg Val Ala Asp Lys Val Arg Lys Arg Lys Val Asp Glu Gly
        450                 455                 460
Ala Gly Asp Ser Ala Ala Val Ala Ser Gly Gly Ala Gln Thr Leu Ala
465                 470                 475                 480
Leu Ala Gly Ser Pro Ala Pro Ser Gly His Pro Lys Ala Gly His Ser
                485                 490                 495
Glu Asn Gly Val Glu Glu Asp Thr Glu Gly Arg Thr Gly Pro Lys Glu
                500                 505                 510
Gly Thr Pro Gly Ser Pro Ser Glu Thr Pro Gly Pro Ser Pro Ala Gly
            515                 520                 525
Pro Ala Gly Asp Glu Pro Ala Glu Ser Pro Ser Glu Thr Pro Gly Pro
        530                 535                 540
Arg Pro Ala Gly Pro Ala Gly Asp Glu Pro Ala Glu Ser Pro Ser Glu
545                 550                 555                 560
Thr Pro Gly Pro Ser Pro Ala Gly Pro Thr Arg Asp Glu Pro Ala Glu
                565                 570                 575
Ser Pro Ser Glu Thr Pro Gly Pro Arg Pro Ala Gly Pro Ala Gly Asp
                580                 585                 590
Glu Pro Ala Glu Ser Pro Ser Glu Thr Pro Gly Pro Arg Pro Ala Gly
            595                 600                 605
Pro Ala Gly Asp Glu Pro Ala Glu Ser Pro Ser Glu Thr Pro Gly Pro
        610                 615                 620
Ser Pro Ala Gly Pro Thr Arg Asp Glu Pro Ala Lys Ala Gly Glu Ala
625                 630                 635                 640
Ala Glu Leu Gln Asp Ala Glu Val Glu Ser Ser Ala Lys Ser Gly Lys
                645                 650                 655
```

-continued

Pro

<210> SEQ ID NO 13
<211> LENGTH: 1232
<212> TYPE: DNA
<213> ORGANISM: Homo sapiens
<220> FEATURE:
<221> NAME/KEY: unsure
<222> LOCATION: (51)
<223> OTHER INFORMATION: n is unsure

<400> SEQUENCE: 13

```
tagaattcag cggccgctga attctagccg agcatggacg accccgactg ncgactccac      60
ctgggaggag gacgaggagg atgcggagga cgcggaggac gaggactgcg aggacggcga     120
ggccgccggc gcgagggacg cggacgcagg ggacgaggac gaggagtcgg aggagccgcg     180
ggcggcgcgg cccagctcgt tccagtccag aatgacaggg tccagaaaact ggcgagccac     240
gagggacatg tgtaggtatc ggcacaacta tccggatctg gtggaacgag actgcaatgg     300
ggacacgcca aacctgagtt tctacagaaa tgagatccgc ttcctgccca acggctgttt     360
cattgaggac attcttcaga actggacgga caactatgac ctccttgagg acaatcactc     420
ctacatccag tggctgtttc ctctgcgaga accaggagtg aactggcatg ccaagccccct     480
cacgctcagg gaggtcgagg tgtttaaaag ctcccaggag atccaggagc ggcttgtccg     540
ggcctacgag ctcatgctgg gcttctacgg gatccggctg gaggaccgag gcacgggcac     600
ggtgggccga gcacagaact accagaagcg cttcagaacc tgaactggcg cagccacaac     660
aacctccgca tcacacgcat cctcaagtcg ccgtgtgagc tgagcctcga gcacttccag     720
gcgccactgg tccgcttctt cctggaggag acgctggtgc ggcgggagct gccgggggtg     780
cggcagagtg ccctggacta cttcatgttc gccgtgcgct gccgacacca gcgccgccag     840
ctggtgcact tcgcctggga gcacttccgg ccccgctgca gttcgtctct ggggccccaa     900
gacaagctgc ggaggttcaa gcccagctct ctgccgcatc cgctcgaggg ctccaggaag     960
gtggaggagg aaggacctgc aggggacgag ccagccgaga gcccatcgga gcccccaggc    1020
cccagcccgg caggacctac aagggatgag ccagccaagg cgggggaggc agaagcctgc    1080
tgcctggctg tgtcttccca cccagctctc ccctgcgccc ctgtctttgt taatcgaccc    1140
ttctggagcg gggggcggcg ggcagggctt gcctttctta gtctgatgcc aagcaaggcc    1200
ttttctgaat aaattcattt gactttcgaa aa                                  1232
```

<210> SEQ ID NO 14
<211> LENGTH: 392
<212> TYPE: PRT
<213> ORGANISM: Homo sapiens

<400> SEQUENCE: 14

Met Asp Asp Pro Asp Cys Asp Ser Thr Trp Glu Glu Asp Glu Glu Asp
1               5                   10                  15

Ala Glu Asp Ala Glu Asp Glu Asp Cys Glu Asp Gly Glu Ala Ala Gly
                20                  25                  30

Ala Arg Asp Ala Asp Ala Gly Asp Glu Asp Glu Glu Ser Glu Glu Pro
            35                  40                  45

Arg Ala Ala Arg Pro Ser Ser Phe Gln Ser Arg Met Thr Gly Ser Arg
        50                  55                  60

Asn Trp Arg Ala Thr Arg Asp Met Cys Arg Tyr Arg His Asn Tyr Pro
65                  70                  75                  80

-continued

```
Asp Leu Val Glu Arg Asp Cys Asn Gly Asp Thr Pro Asn Leu Ser Phe
                 85                  90                  95
Tyr Arg Asn Glu Ile Arg Phe Leu Pro Asn Gly Cys Phe Ile Glu Asp
            100                 105                 110
Ile Leu Gln Asn Trp Thr Asp Asn Tyr Asp Leu Leu Glu Asp Asn His
        115                 120                 125
Ser Tyr Ile Gln Trp Leu Phe Pro Leu Arg Glu Pro Gly Val Asn Trp
    130                 135                 140
His Ala Lys Pro Leu Thr Leu Arg Glu Val Glu Val Phe Lys Ser Ser
145                 150                 155                 160
Gln Glu Ile Gln Glu Arg Leu Val Arg Ala Tyr Glu Leu Met Leu Gly
                165                 170                 175
Phe Tyr Gly Ile Arg Leu Glu Asp Arg Gly Thr Gly Thr Val Gly Arg
            180                 185                 190
Ala Gln Asn Tyr Gln Lys Arg Phe Gln Asn Leu Asn Trp Arg Ser His
        195                 200                 205
Asn Asn Leu Arg Ile Thr Arg Ile Leu Lys Ser Pro Cys Glu Leu Ser
    210                 215                 220
Leu Glu His Phe Gln Ala Pro Leu Val Arg Phe Leu Glu Glu Thr
225                 230                 235                 240
Leu Val Arg Arg Glu Leu Pro Gly Val Arg Gln Ser Ala Leu Asp Tyr
                245                 250                 255
Phe Met Phe Ala Val Arg Cys Arg His Gln Arg Arg Gln Leu Val His
            260                 265                 270
Phe Ala Trp Glu His Phe Arg Pro Arg Cys Lys Phe Val Trp Gly Pro
        275                 280                 285
Gln Asp Lys Leu Arg Arg Phe Lys Pro Ser Ser Leu Pro His Pro Leu
    290                 295                 300
Glu Gly Ser Arg Lys Val Glu Glu Gly Pro Ala Gly Asp Glu Pro
305                 310                 315                 320
Ala Glu Ser Pro Ser Glu Thr Pro Gly Pro Ser Pro Ala Gly Pro Thr
                325                 330                 335
Arg Asp Glu Pro Ala Lys Ala Gly Glu Ala Glu Ala Cys Cys Leu Ala
            340                 345                 350
Val Ser Ser His Pro Ala Leu Pro Cys Ala Pro Val Phe Val Asn Arg
        355                 360                 365
Pro Phe Trp Ser Gly Gly Arg Arg Ala Gly Leu Ala Phe Leu Ser Leu
    370                 375                 380
Met Pro Ser Lys Ala Phe Ser Glu
385                 390
```

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:antisense
      primer for rat OGFr

<400> SEQUENCE: 15
gactcaggga cttagcttca tcc                                           23

<210> SEQ ID NO 16
<211> LENGTH: 23
<212> TYPE: DNA
<213> ORGANISM: Artificial Sequence -continued

```
<220> FEATURE:
<223> OTHER INFORMATION: Description of Artificial Sequence:scrambled
      primer

<400> SEQUENCE: 16
atagatacta cgccggctgt cct                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:antisense
      primer for human OGFr

<400> SEQUENCE: 17
ggtcgtccat gctcggctag aat                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:scrambled
      primer

<400> SEQUENCE: 18
gtgcagtgca atgctctccg tga                                            23
```